United States Patent [19]

Bartmann et al.

[11] Patent Number: 5,679,285

[45] Date of Patent: Oct. 21, 1997

[54] VINYLENE COMPOUNDS AND LIQUID-CRYSTALLINE MEDIUM

[75] Inventors: Ekkehard Bartmann, Erzhausen; Sabine Schoen, Darmstadt; Kazuaki Tarumi, Seeheim-Jugenheim, all of Germany

[73] Assignee: Merck Patent Gesellschaft mit beschrankter Haftung, Darmstadt, Germany

[21] Appl. No.: 602,063

[22] Filed: Feb. 15, 1996

[30] Foreign Application Priority Data

Feb. 16, 1995 [DE] Germany .................. 195 05 189.0

[51] Int. Cl.[6] .................. C09K 19/30; C09K 19/34; C09K 19/32; C07C 19/08
[52] U.S. Cl. .................. 252/299.63; 252/299.61; 252/299.2; 570/127; 560/60; 560/65; 568/642; 546/339; 549/369; 544/298
[58] Field of Search .................. 252/299.63, 299.01, 252/299.6; 546/339; 560/60, 65; 568/642; 549/369; 544/298; 570/127

[56] References Cited

U.S. PATENT DOCUMENTS

| | | | |
|---|---|---|---|
| 5,055,220 | 10/1991 | Uchida et al. | 252/299.01 |
| 5,204,018 | 4/1993 | Kelly | 252/299.63 |
| 5,308,537 | 5/1994 | Coates et al. | 252/299.6 |
| 5,358,662 | 10/1994 | Hirose et al. | 252/299.63 |
| 5,370,822 | 12/1994 | Matsui et al. | 252/299.63 |
| 5,380,462 | 1/1995 | Kelly et al. | 252/299.63 |
| 5,523,127 | 6/1996 | Ohnishi et al. | 428/1 |
| 5,534,187 | 7/1996 | Miyazawa et al. | 252/299.01 |

FOREIGN PATENT DOCUMENTS

6/20443 3/1994 Japan.

*Primary Examiner*—C. H. Kelly
*Attorney, Agent, or Firm*—Millen, White, Zelano & Branigan, P.C.

[57] ABSTRACT

Vinylene compounds of the formula I

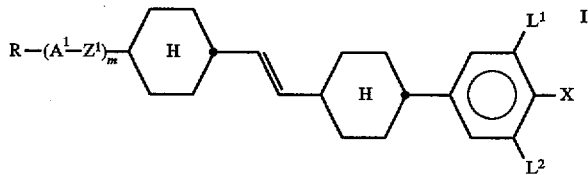

in which $R, A^1, Z^1, X, L^1, L^2$ and m have the meaning given in claim 1 are suitable as components of liquid-crystalline media.

20 Claims, No Drawings

VINYLENE COMPOUNDS AND LIQUID-CRYSTALLINE MEDIUM

The invention relates to novel vinylene compounds of the formula I

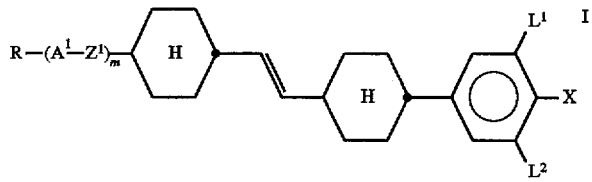

in which

R is an alkenyl radical having 2 to 15 carbon atoms which is unsubstituted, monosubstituted by CN or $CF_3$ or monosubstituted to perhalo-substituted by halogen, in which radicals one groups may also in each case independently of one another be replaced by —O—, —S—,

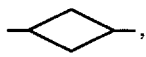

—CO—, —CO—O, —O—CO— or —O—CO—O— in such a way that oxygen atoms are not linked directly to one another, $A^1$ (a) is a trans-1,4-cyclohexylene radical in which one or more non-adjacent $CH_2$ groups may be replaced by —O— and/or —S—, (b) is a 1,4-phenylene radical in which one or two CH groups may be replaced by N, or (c) is a radical selected from the group consisting of 1,4-cyclohexenylene, 1,4-bicyclo[2.2.2]-octylene, piperidine-1,4-diyl, naphthalene-2,6-diyl, decahydronaphthalene-2,6-diyl and 1,2,3,4-tetrahydronaphthalene-2,6-diyl where the radicals (a) and (b) can be substituted one or more times by CN or fluorine, $Z^1$ is —CO—O—, —O—CO—, —$CH_2$O—, —O$CH_2$—, —$CH_2CH_2$—, —CH=CH—, —C≡C— or a single bond, X is CN, OCN, NCS, Cl, F or halogenated alkyl or alkenyl having 1 to 7 carbon atoms, in which one or more non-adjacent $CH_2$ groups may also be replaced by —O—, is 0 or 1, and $L^1$ and $L^2$ are each independently H or F.

The invention relates furthermore to the use of these compounds as components of liquid-crystalline media and to liquid-crystal and electrooptical display elements which comprise the liquid-crystalline media according to the invention.

The compounds of the formula I can be used as components of liquid-crystalline media, especially for displays based on the principle of the twisted cell, on the guest-host effect, on the effect of the deformation of aligned phases or on the effect of dynamic scattering, for example.

An object of the invention was to discover novel, stable, liquid-crystalline or mesogenic compounds which are suitable as components of liquid-crystalline media and at the same the possess, in particular, comparatively low viscosity and a relatively high dielectric anisotropy.

Upon further study of the specification and appended claims, further objects and advantages of this invention will become apparent to those skilled in the art.

Compounds of the formula

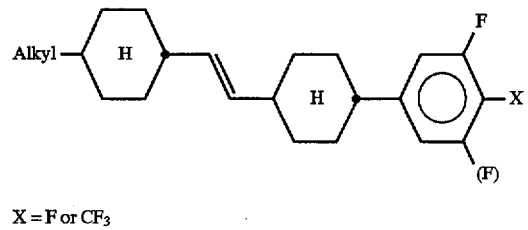

X = F or $CF_3$ are already known from U.S. Pat. No. 5,358,662 and WO 94/20443.

It has now been found that compounds of the formula I are pre-eminently suitable as components of liquid-crystalline media. In particular, they have comparatively low viscosities. They can be used to obtain stable liquid-crystalline media having a broad mesophase range and advantageous values for the optical and dielectric anisotropy. These media, in addition, have very good low-temperature characteristics.

In view of the very different applications of such compounds of high Δε, however, it was desirable to have further available compounds which have properties tailored precisely to the respective applications.

The provision of compounds of the formula I also, quite generally, extends considerably the range of liquid-crystalline substances which are suitable, from a variety of applications-related standpoints, for the preparation of liquid-crystalline mixtures.

The compounds of the formula I possess a broad range of application. Depending on the selection of the substituents, these compounds can be used as base materials from which liquid-crystalline media are pre-dominantly composed. It is also possible, however, to add liquid-crystalline base materials from other classes of compounds to the compounds of the formula I in order, for example, to influence the dielectric and/or optical anisotropy of such a dielectric and/or to optimize its threshold voltage and/or its viscosity.

In the pure state, the compounds of the formula I are colorless and form liquid-crystalline mesophases in a temperature range which is situated at a favorable level for their electrooptical use. Chemically, thermally and with respect to light, they are stable.

The invention therefore provides the compounds of the formula I and provides the use of these compounds as components of liquid-crystalline media. The invention additionally provides liquid-crystalline media containing at least one compound of the formula I, and liquid-crystal display elements, especially electrooptical display elements, comprising such media.

In the compounds of the formula I, R is preferably a straight-chain alkenyl radical, and $A^1$ is preferably Phe or Cyc, or Che, Pyr or Dio, wherein Phe is 1,4-phenylene, Cyc is trans-1,4-cyclohexylene, Che is 1,4-cyclohexenylene, Pyr is pyridine-2,5-diyl and Dio is trans-1,3-dioxane-2,5-diyl.

Preference is also given to compounds of the formula I and of all subformulae in which $A^1$ is 1,4-phenylene which is mono- or disubstituted by F or mono-substituted by CN. In particular these are 2-fluoro-1,4-phenylene, 3-fluoro-1,4-phenylene and 3,5-difluoro-1,4-phenylene, and 2-cyano-1,4-phenylene and 3-cyano-1,4-phenylene.

$Z^1$ is preferably a single bond, —CO—O—, —O—CO— or —$CH_2CH_2$—, and secondarily is preferably —$CH_2$O— or —O$CH_2$—.

The alkenyl radical R can be straight-chain branched. It is preferably straight-chain and has 2 to 10 carbon atoms. Accordingly, it is in particular vinyl, prop-1- or prop-2-enyl, but-1-, -2- or but-3-enyl, pent-1-, -2-, -3- or pent-4-enyl, hex-1-, -2-, -3-, -4- or hex-5-enyl, hept-1-, -2-, -3-, -4-, -5- or hept-6-enyl,. oct-1-, -2-, -3-, -4-, -5-, -6- or oct-7-enyl, non-1-, -2-, -3-, -4-, -5-, -6-, -7- or non-8-enyl, dec-1-, -2-, -3-, -4-, -5-, -6-, -7-, -8-or dec-9-enyl, for example.

If R is an alkenyl radical which is monosubstituted by CN or $CF_3$, this radical is preferably straight-chain and the substitution by CN or $CF_3$ is in the ω-position.

In the compounds of the the formula I, preferred stereoisomers are those in which the rings Cyc and piperidine are trans-1,4-disubstituted. Those of the abovementioned formulae which contain one or more groups Pyd, Pyr and/or Dio embrace in each case the two 2,5 positional isomers.

Some very particularly preferred, smaller groups of compounds are those of subformulae I1 to I3 [$L^1$, $L^2$: H or F; $R^1$=H, ethyl, methyl or propyl; n=0–3]:

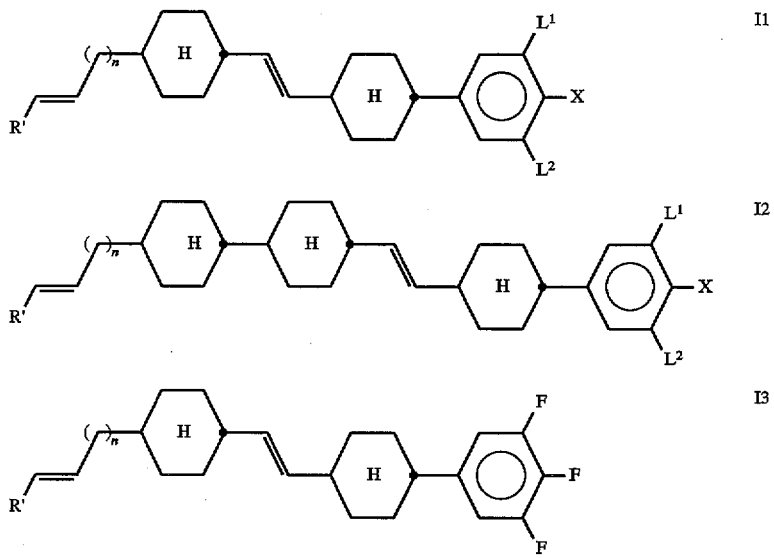

If R is an alkenyl radical which is at least monosubstituted by halogen, this radical is preferably straight-chain and halogen is preferably F or Cl. In the case of polysubstitution, halogen is preferably F. The resulting radicals also include perfluorinated radicals. In the case of monosubstitution, the fluorine or chlorine substituent can be in any desired position, but preferably in the ω-position.

Compounds of the formula I which have a wing group R suitable for polymerization reactions are themselves suitable for preparing liquid-crystalline polymers.

Compounds of the formula I having a branched wing group. R can occasionally be of importance owing to better solubility in the customary liquid-crystalline base materials, but especially as chiral dopants, if they are optically active. Smectic compounds of this kind are suitable as components for ferroelectric materials. Branched groups of this kind generally contain not more than one chain branching point.

Compounds of the formula I having $S_\lambda$ phases are suitable, for example, for thermally addressed displays.

Compounds of the formula I which have a wing group R suitable for polycondensation reactions are themselves suitable for preparing liquid-crystalline polycondensation products.

Formula I embraces both the racemates of these compounds and the optical isomers and mixtures thereof.

Among these compounds of the formula I and the subformulae, preferred compounds are those in which at least one of the radicals present therein has one of the preferred definitions stated.

Preference is given to compounds of the formulae I1 and I2 in which at least one of the radicals $L^1$ and $L^2$ is fluorine. Particular preference is given to compounds of the formula I in which $L^1=L^2=F$.

The alkenyl radical is preferably a group $(CH_2)_n$—CH=CH—R'— in which n=0–3 and R' is H or alkyl having 1–5 carbon atoms, preferably $CH_3$ and $C_2H_5$.

X is preferably F, $OCF_3$ or halogenated alkyl, alkoxy or alkenyl having 1 to 3 carbon atoms. Halogenated preferably means fluorinated.

X is in particular F, Cl, $CHF_2$, $OCF_3$, $OCHF_2$, $CH=CF_2$, $CF=CF_2$, $CF=CHF$, $CCl=CClF$, $CH=CHCl$, $CH=CH-CF_3$, $OCH=CF_2$, $OCF=CF_2$, $OCF=CHF$, $OCH=CH-CF_3$, $OCH_2CF_3$, $C_2F_4H$, $C_2F_5$, $OC_2F_4H$, $OC_2F_5$, and $(CH_2)_nCF_3$, $O(CH_2)_nCF_3$, $(CH_2)_nCH_2F$, $(CH_2)_nCF_2H$, $O(CH_2)_nCHF_2$, $O(CH_2)_nCH=CF_2$, $O(CH_2)_nCF=CF_2$, $C_3F_7$, $OC_3F_7$, where n is 1 to 5, for example.

The compounds of the formula I are prepared by methods which are known per se as are described in the literature (e.g. in the standard works such as Houben-Weyl, Methoden der Organischen Chemie [Methods of Organic Chemistry], Georg-Thieme-Verlag, Stuttgart), under reaction conditions which are known and suitable for the reactions mentioned.

In these reactions, use may also be made of variants which are known per se and are not mentioned in any more detail here.

Compounds according to the invention can be prepared, for example, by reacting benzene derivatives according to the following reaction schemes:

Scheme 1
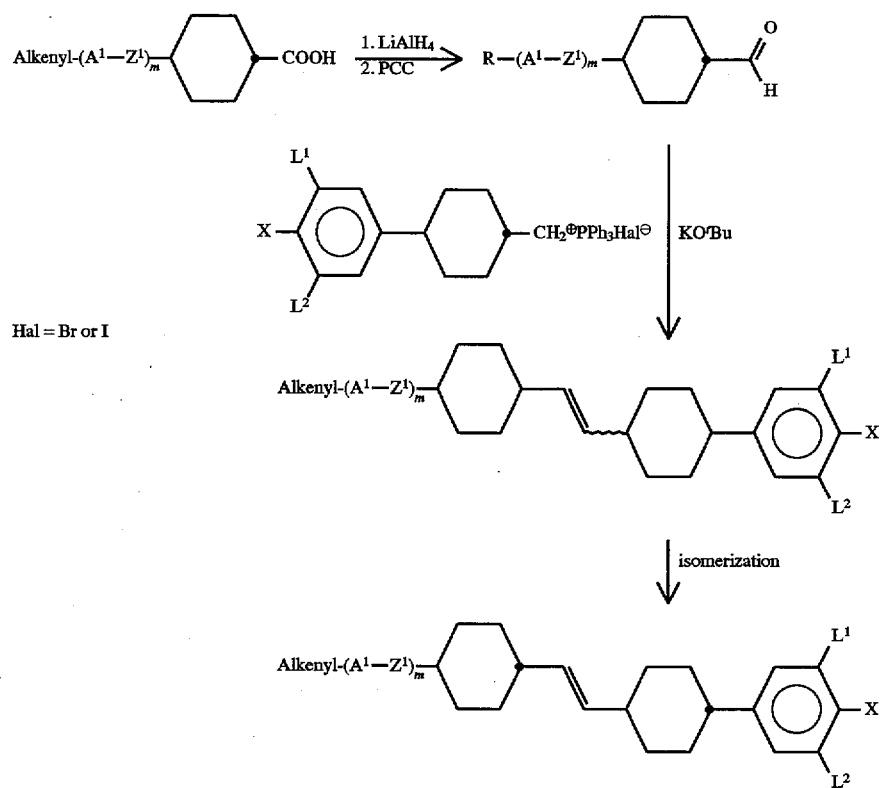
Hal = Br or I
Scheme 2
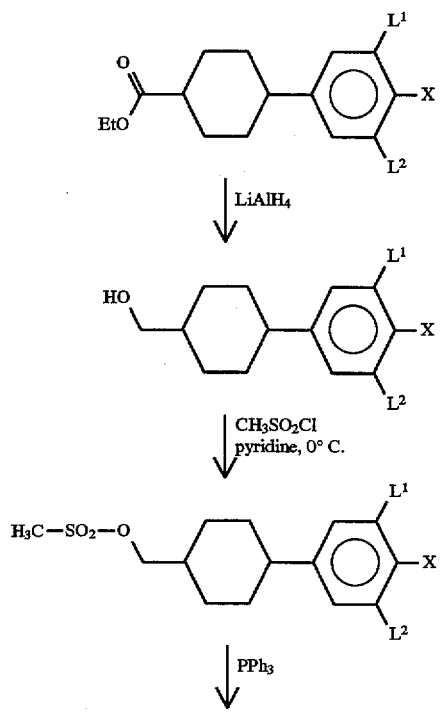

-continued
Scheme 2
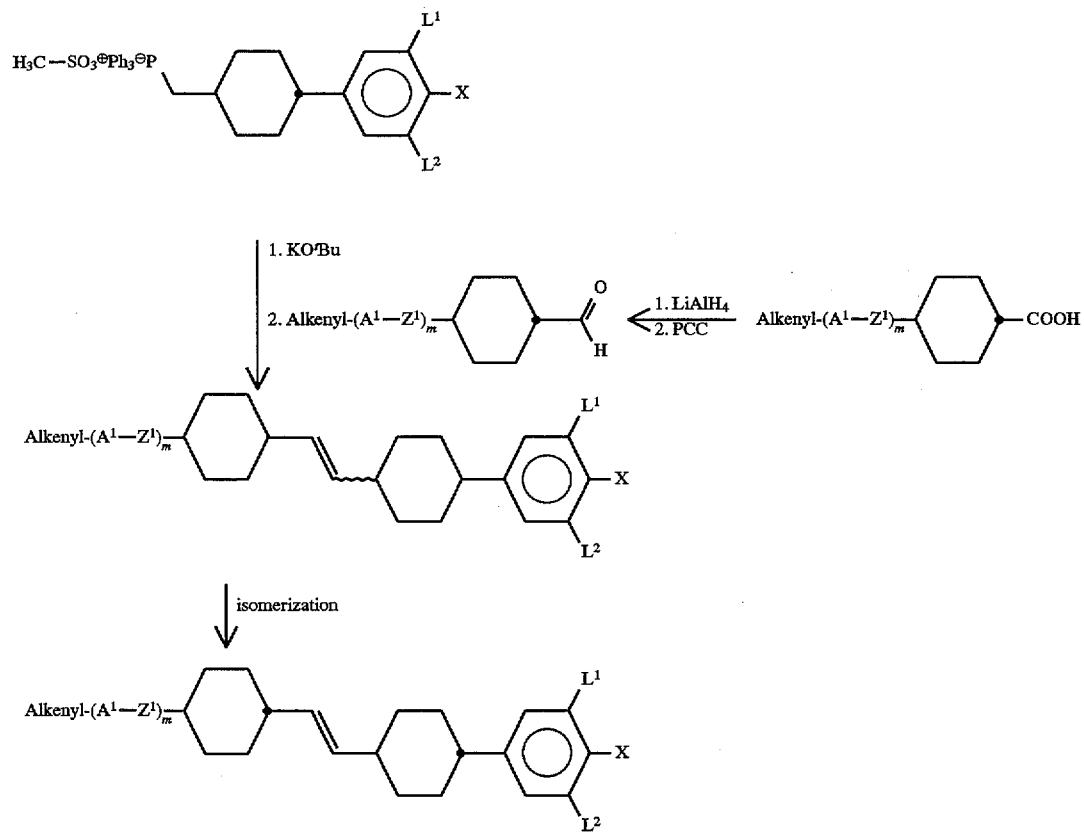
Scheme 3
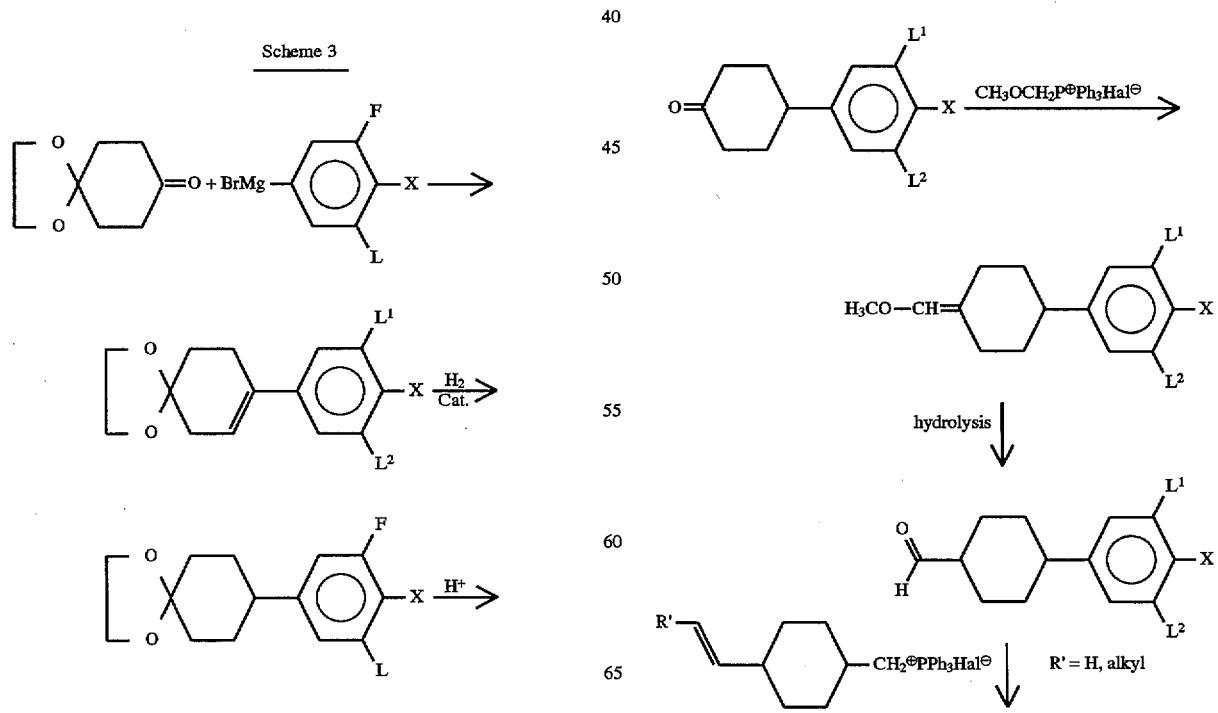

-continued
Scheme 3

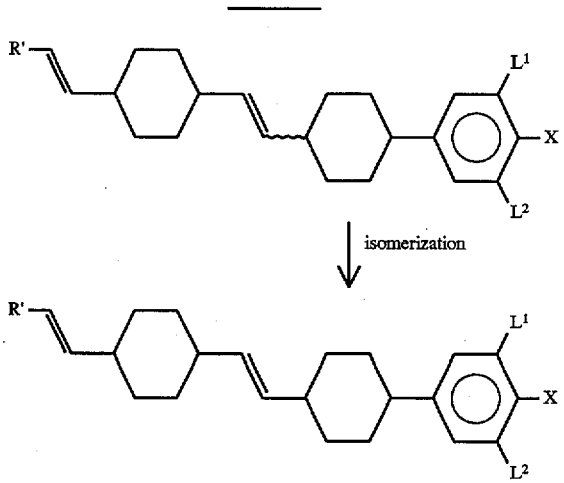

Scheme 4

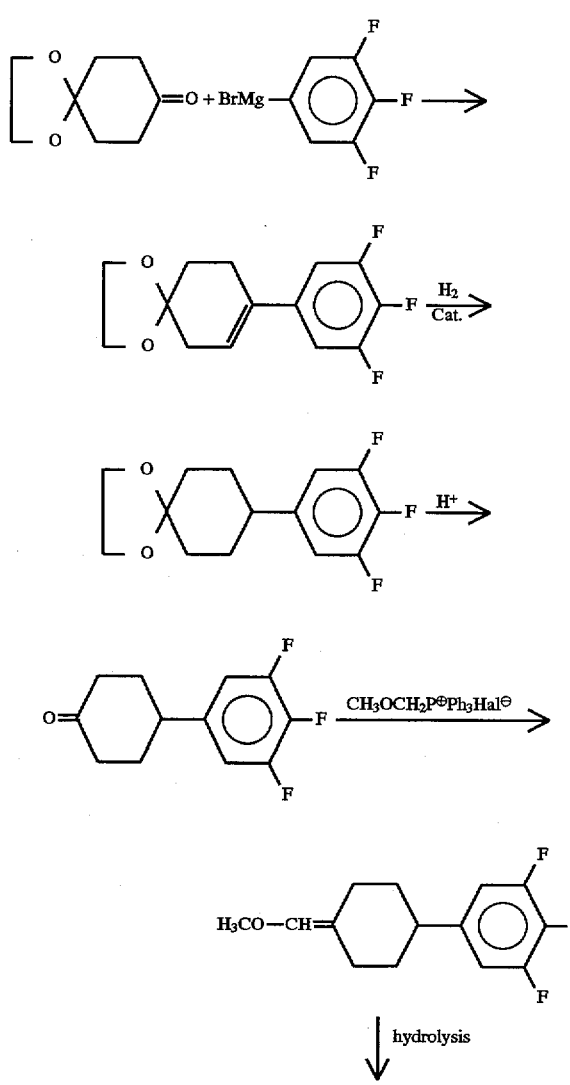

-continued
Scheme 4

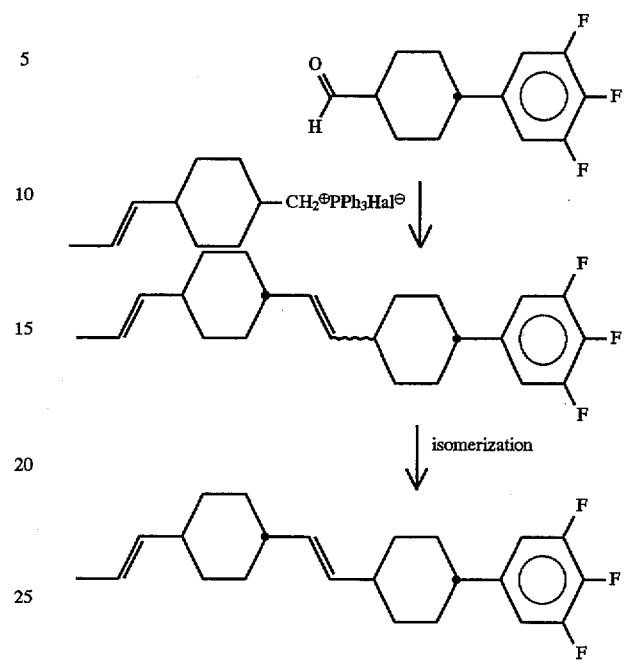

The invention also provides electrooptical displays (especially STN or MLC displays with two plane-parallel backing plates which, with an edging, form a cell, integrated nonlinear elements for switching individual pixel cells on the backing plates, and a nematic liquid-crystal mixture which is located in the cell and has positive dielectric anisotropy and a high specific resistance) which comprise such media and for the use of these media for electrooptical purposes.

The liquid-crystal mixtures according to the invention enable a significant expansion of the sphere of parameters available.

The combinations which can be achieved of clearing point, low-temperature viscosity, thermal stability, UV stability and dielectric anisotropy go far beyond previous materials from the prior art.

The requirement for high clearing point, a nematic phase at low temperature and a high $\Delta\epsilon$ was not fully met until now. Systems such as ZLI-3119, for example, although having a comparable clearing point and comparably favorable viscosities, only possess a $\Delta\epsilon$ of +3.

Other mixture systems possess comparable viscosities and values for $\Delta\epsilon$, but only have clearing points in the region of 60° C.

The liquid-crystal mixtures according to the invention make it possible, for example, to retain the nematic phase down to −20° C. and preferably down to −30° C., particularly preferably down to −40° C., obtain clearing points above 80° C., preferably above 90° C., particularly preferably above 100° C., coupled with dielectric anisotropy values $\Delta\epsilon \geq 6$, preferably $\geq 8$, and a high value for the specific resistance, thereby enabling outstanding STN and MLC displays to be obtained. The mixtures are characterized in particular by low operating voltages. The TN thresholds are below 2.0V, preferably below 1.5V, particularly preferably <1.3V.

It is self-evident that, by appropriately choosing the components of the mixtures according to the invention, it is also possible to realize higher clearing points (e.g. above 110° C.) at higher threshold voltages or lower clearing points at lower threshold voltages while retaining the other advantageous properties. Similarly, given an appropriately low increase in viscosities, mixtures of greater Δε and thus lower thresholds can be obtained. The MLC displays according to the invention preferably operate in the first transmission minimum according to Gooch and Tarry [C. H. Gooch and H. A. Tarry, Electron. Lett. 10, 2–4, 1974; C. H. Gooch and H. A. Tarry, Appl. Phys., Vol. 8, 1575–1584, 1975], in which case here, in addition to particularly favorable electrooptical properties, for example great steepness of the characteristic line and low angular dependence of the. contrast (DE-C 30 22 818), and at the same threshold voltage as in an analogous display, in the second minimum a smaller dielectric anisotropy is sufficient. It is hereby possible, using the mixtures according to the invention, to realize substantially higher specific resistances in the first minimum than in the case of mixtures comprising cyano compounds. By appropriate choice of the individual components and their proportions by weight, using simple routine methods, the person skilled in the art can establish the birefringence which is required for a predetermined layer thickness of the MLC display.

The viscosity at 20° C. is preferably<60 mPa.s, particularly preferably<50 mPa.s. The nematic phase range is preferably at least 90° C, in particular at least 100° C. This range preferably extends at least from −20° to +80°.

Measurements of the capacity holding ratio (HR) [S. Matsumoto et al., Liquid Crystals 5, 1320 (1989); K. Niwa et al., Proc. SID Conference, San Francisco, June 1984, p. 304 (1984); G. Weber et al., Liquid Crystals 5, 1381 (1989)] have shown that mixtures according to the invention comprising compounds of the formula I have a much lower drop in HR with rising temperature than analogous mixtures comprising, instead of the compounds of the formula I, cyanophenylcyclohexanes of the formula

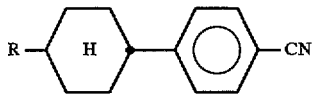

or esters of the formula

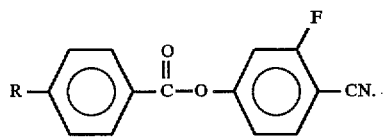

The UV stability of the mixtures according to the invention is also considerably better, i.e. they show a much lower reduction in HR under UV exposure.

The media according to the invention are preferably based on a plurality of (preferably two or more) compounds of the formula I, i.e. the proportion of these compounds is 5–95%, preferably 10–60% and, with particular preference, in the range of 20–50%.

The individual compounds of the formulae I to XI and subformulae thereof which can be used in the media according to the invention are either known or can be prepared in an analogous manner to known compounds.

Preferred embodiments are indicated below:

Medium contains in addition one or more compounds selected from the group consisting of the general formulae II to VI:

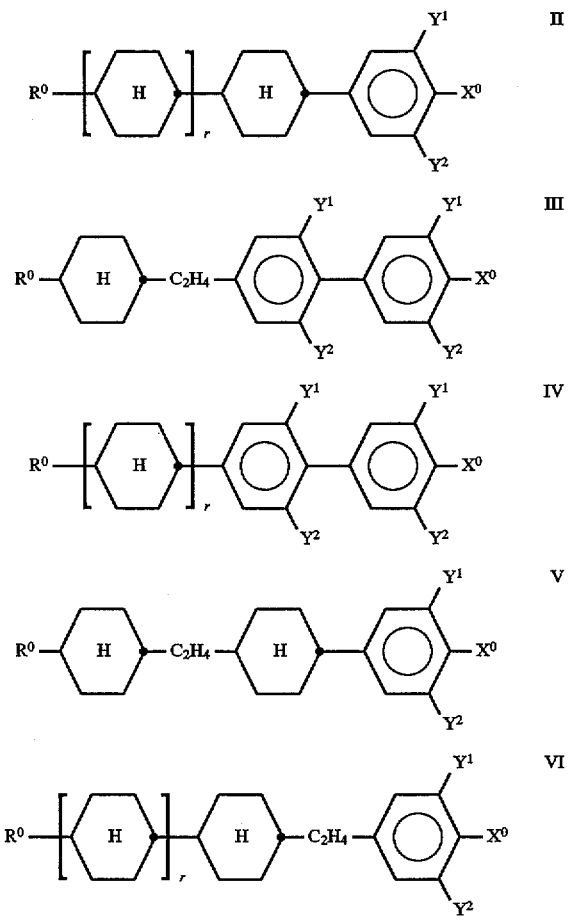

in which the individual radicals have the following definitions:

$R^0$: n-alkyl, oxaalkyl, fluoroalkyl or alkenyl having in each case 1 to 9 carbon atoms $X^0$: F, Cl, halogenated alkyl, alkenyl or alkoxy having 1 to 6 carbon atoms $Y^1$ and $Y^2$: each independently H or F r: 0 or 1.

The compound of the formula IV is preferably

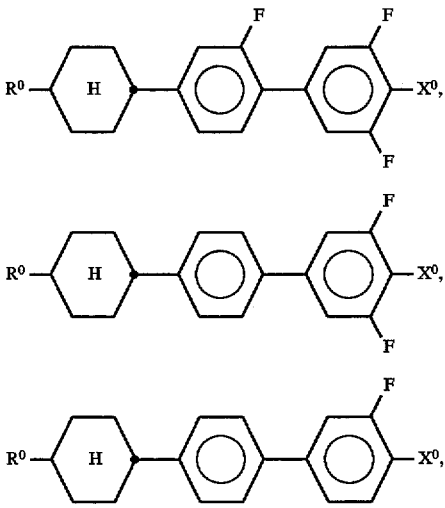

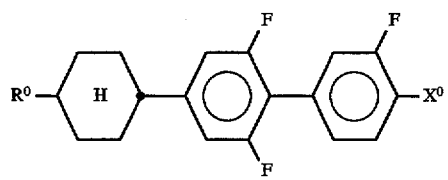

or

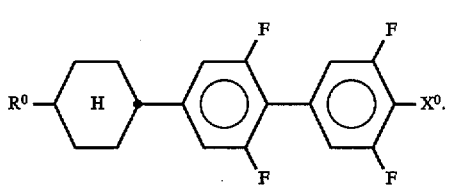

Medium additionally contains one or more compounds of the formulae

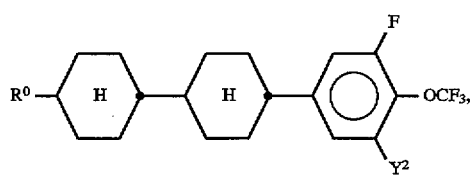

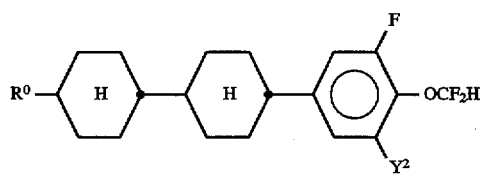

and/or

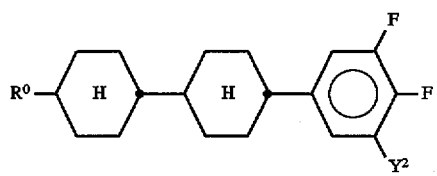

Medium additionally contains one or more compounds selected from the group consisting of the general formulae VII to XII:

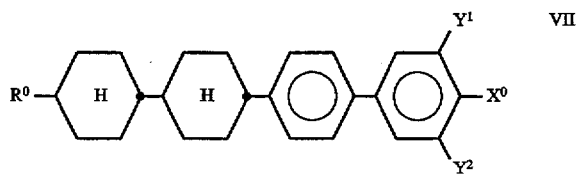    VII

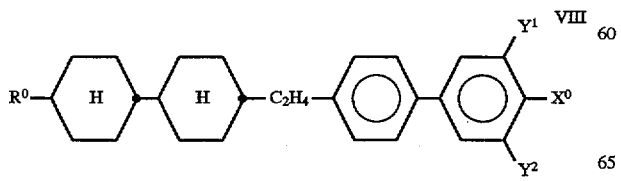    VIII

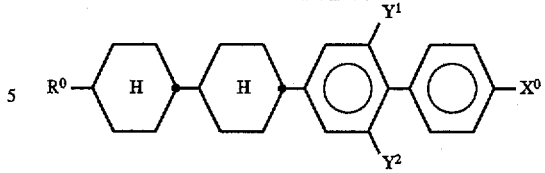    IX

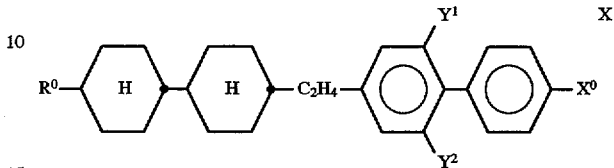    X

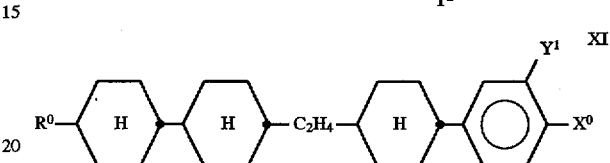    XI

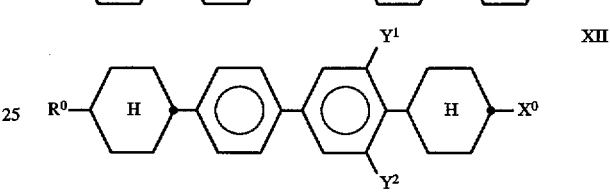    XII in which $R^0$, $X^0$, $Y^1$ and $Y^2$ in each case independently of one another have one of the meanings given in above.

The proportion of compounds of the formulae I to VI together in the overall mixture is at least 50% by weight;

the proportion of compounds of the formula I in the overall mixture is from 5 to 50% by weight;

the proportion of compounds of the formulae II to VI in the overall mixture is from 30 to 70% by weight; and

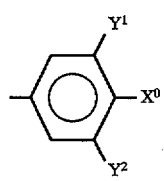

is preferably

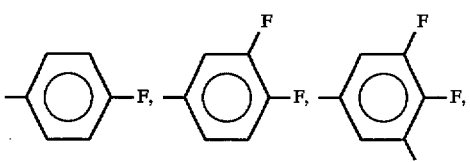

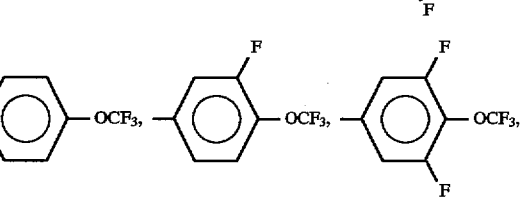

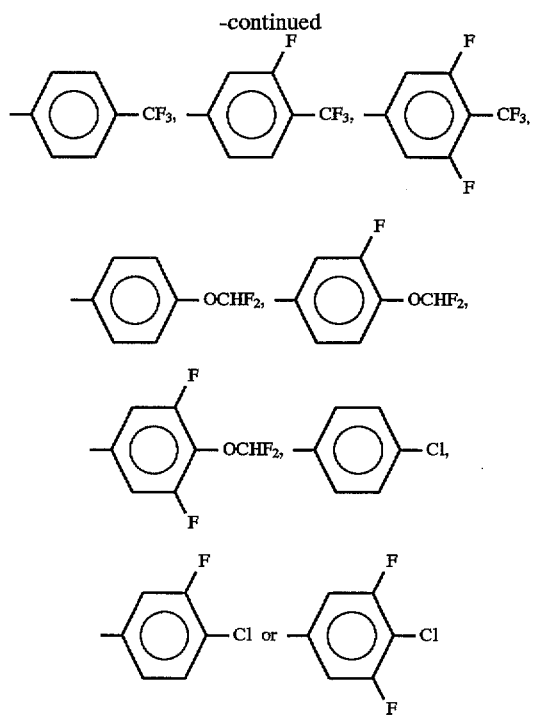

the medium comprises compounds of the formulae II, III, IV, V or VI $R^0$ is straight-chain alkyl or alkenyl having 2 to 7 carbon atoms the medium consists essentially of compounds of the formulae I to VI the medium comprises further compounds, preferably selected from the following group consisting of the general formulae XIII to XVI:

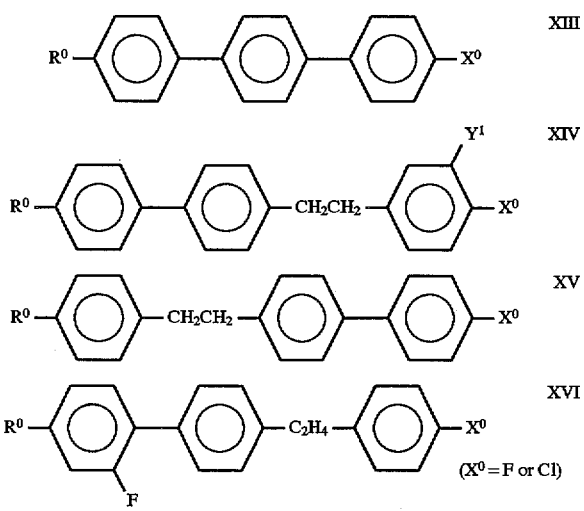

in which $R^0$ and $X^0$ have the meaning given above and the 1,4-phenylene rings can be substituted by CN, chlorine or fluorine. The 1,4-phenylene rings are preferably mono- or polysubstituted by fluorine atoms.

The weight ratio I: (II+III+IV+V+VI) is preferably from 1:10 to 10:1.

Medium consists essentially of compounds selected from the group consisting of the general formulae I to XII.

It has been found that even a relatively low proportion of compounds of the formula I mixed with the customary liquid-crystal materials, but especially with one or more compounds of the formulae II, III, IV, V and/or VI, leads to a considerable reduction in the threshold voltage and to low values for the birefringence, with broad nematic phases having low smectic/nematic transition temperatures being observed at the same time, thus improving the stability on storage. The compounds of the formulae I to VI are colorless, stable and can be mixed readily with one another and with other liquid-crystal materials.

The term alkyl herein preferably comprises straight-chain and branched alkyl groups having 1–7 carbon atoms, especially the straight-chain groups methyl, ethyl, propyl, butyl, pentyl, hexyl and heptyl. Groups having 2–5 carbon atoms are generally preferred.

The term alkenyl herein preferably comprises straight-chain and branched alkenyl groups having 2–7 carbon atoms, especially the straight-chain groups. Alkenyl groups are in particular $C_2$–$C_7$-1E-alkenyl, $C_4$–$C_7$-3E-alkenyl, $C_5$–$C_7$-4-alkenyl, $C_6$–$C_7$-5-alkenyl and $C_7$-6-alkenyl, especially $C_2$–$C_7$-1E-alkenyl, $C_4$–$C_7$-3E-alkenyl and $C_5$–$C_7$-4-alkenyl. Examples of preferred alkenyl groups are vinyl, 1E-propenyl, 1E-butenyl, 1E-pentenyl, 1E-hexenyl, 1E-heptenyl, 3-butenyl, 3E-pentenyl, 3E-hexenyl, 3E-heptenyl, 4-pentenyl, 4Z-hexenyl, 4E-hexenyl, heptenyl, 5-hexenyl, 6-heptenyl and the like. Groups having up to 5 carbon atoms are generally preferred.

The term fluoroalkyl comprises preferably straight-chain groups with terminal fluorine, i.e. fluoromethyl, 2-fluoroethyl, 3-fluoropropyl, 4-fluorobutyl, 5-fluoropentyl, 6-fluorohexyl and 7-fluoroheptyl. Other positions of the fluorine, however, are not excluded.

The term oxaalkyl comprises preferably straight-chain radicals of the formula $C_nH_{2n+1}$—O—$(CH_2)_m$, in which n and m are each independently of one another 1 to 6. Preferably, n =1 and m is 1 to 6.

By a suitable choice of the definitions of $R^0$ and $X^0$, it is possible to modify the response times, threshold voltage, steepness of the characteristic transmission lines, etc. in a desired manner. For example, 1E-alkenyl radicals, 3E-alkenyl radicals, 2E-alkenyloxy radicals and the like lead in general to shorter response times, improved nematic tendencies and a higher ratio of the elastic constants $k_{33}$ (bend) and $k_{11}$ (splay) in comparison to alkyl and alkoxy radicals. 4-Alkenyl radicals, 3-alkenyl radicals and the like give rise in general to lower threshold voltages and lower values of $k_{33}/k_{11}$ in comparison to alkyl and alkoxy radicals.

A —$CH_2CH_2$— group leads in general to higher values of $k_{33}/k_{11}$ in comparison to a simple covalent bond. Higher values of $k_{33}/k_{11}$ enable, for example, flatter characteristic transmission lines in TN cells with 90° twisting (in order to obtain grey shades) and steeper characteristic transmission lines in STN, SBE and OMI cells (greater multiplexibility) and vice versa.

The optimum ratio of the compounds of the formulae I and II+III+IV+V+VI depends largely on the desired properties, on the choice of the components of the formulae I, II, III, IV, V and/or VI and on the choice of any other components present. Suitable ratios within the range indicated above can readily be determined from case to case.

The overall quantity of compounds of the formulae I to XII in the mixtures according to the invention is not critical. The mixtures can therefore comprise one or more additional components for the purpose of optimizing various properties. The effect observed on the response times and the threshold voltage, however, is generally greater the higher the overall concentration of compounds of the formulae I to XII.

In a particularly preferred embodiment, the media according to the invention comprise compounds of the formulae II to VI (preferably II and/or III) in which $X^0$ is $OCF_3$, $OCHF_2$, F, $OCH=CF_2$, $OCF=CF_2$ or $OCF_2—CF_2H$. A favorable synergistic effect with the compounds of the formula I leads to particularly advantageous properties.

The invention preferably provides a liquid-crystalline medium based on a mixture of polar compounds having positive dielectric anistropy, characterized in that it comprises one or mote compounds of the formula I and, in addition, one or more compounds of the formulae II to VI, and also .one or more compounds of the, formulae VII to XII. Such media are suitable in particular for MLC displays.

The media according to the invention can additionally comprise a component A consisting of one or more compounds having a dielectric anistropy of from −1.5 to +1.5 of the general formula I'

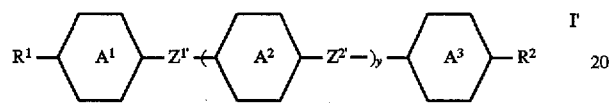

I' in which
$R^1$ and $R^2$ in each case independently of one another are n-alkyl, ω-fluoroalkyl or n-alkenyl having 1 to 9 carbon atoms,
the rings $A^1$, $A^2$, and $A^3$ in each case independently of one another are 1,4-phenylene, 2- or 3-fluoro-1,4-phenylene, trans-1,4-cyclohexylene or 1,4-cyclohexenylene,
$Z^1$ and $Z^2$ in each case independently of one another are —$CH_2CH_2$—, —C≡C—, —CO—O—, —O—CO— or a single bond,
and
y is 0, 1 or 2.

Component A preferably comprises one or more compounds selected from the group consisting of II1 to II7:

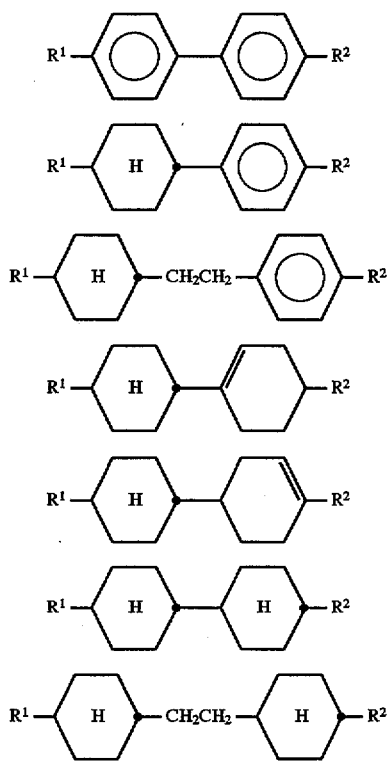

in which $R^1$ and $R^2$ have the meaning given for formula I'.

Preferably, component A additionally comprises one or more compounds selected from the group consisting of II8 to II20:

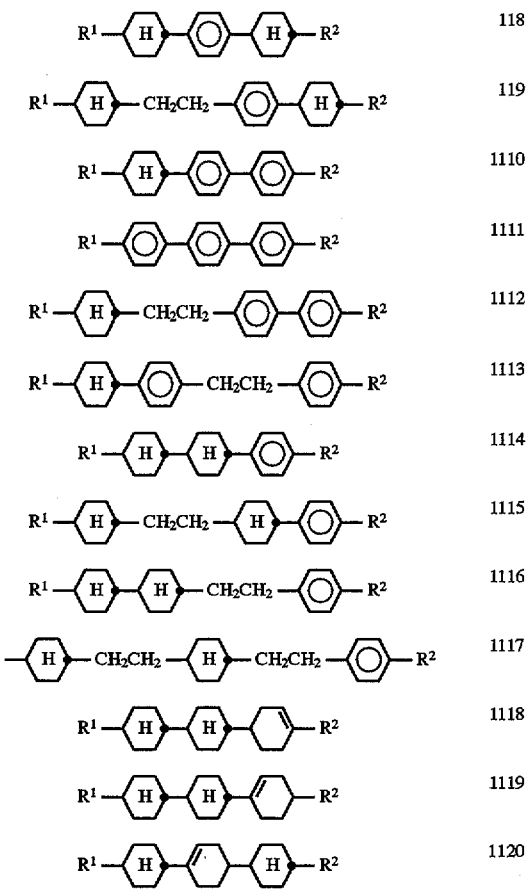

in which $R^1$ and $R^2$ have the meaning given for formula I' and the 1,4-phenylene groups in II8 to II17, in each case independently of one another, can also be substituted one or more times by fluorine.

In addition, component A preferably additionally comprises one or more compounds selected from the group consisting of II21 to II25:

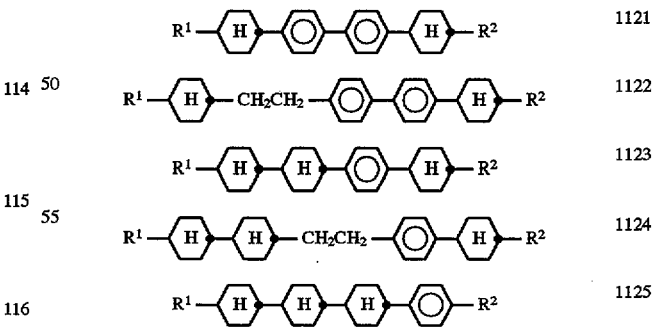

in which $R^1$ and $R^2$ have the meaning given for formula I' and the 1,4-phenylene groups in II21 to II25, in each case independently of one another, can also be substituted one or more times by fluorine.

Finally, preference is given to such mixtures in which component A comprises one or more compounds selected from the group consisting II26 and II27:

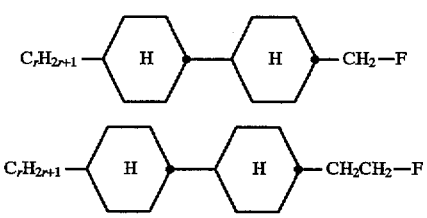

in which $C_4H_{2r+1}$ is a straight-chain alkyl group having 1 to 7 carbon atoms.

In some cases it proves advantageous to add compounds of the formula

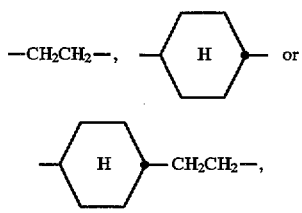

in which $R^1$ and $R^2$ have the meaning given for formula I' and
$Z^0$ is a single bond,

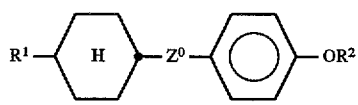

in order to suppress smectic phases, although this can lower the specific resistance. In order to obtain combinations of parameters which are optimal for the application, the person skilled in the art can readily ascertain whether and, if so, in what quantity these compounds can be added. It is normal to use less than 15%, in particular 5–10%, by weight.

Further preference is given to liquid-crystal mixtures which comprise one or more compounds selected from the group consisting of III' and IV':

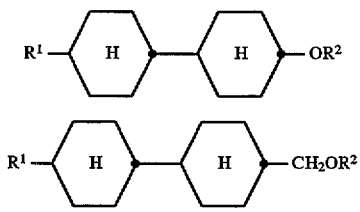

in which $R^1$ and $R^2$ have the meaning given for formula I'.

The nature and quantity of the polar compounds having positive dielectric anisotropy is not critical per se. The person skilled in the art can select suitable materials from a large range of components and base mixtures, which are known and in many cases also commercially available, in simple routine tests. The media according to the invention preferably comprise one more compounds of the formula I"

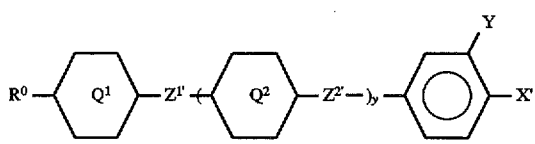

in which $Z^{1'}$, $Z^{2'}$ and y have the meaning given for formula I', $Q^1$ and $Q^2$ in each case independently of one another are 1,4-phenylene, trans-1,4-cyclohexylene or 3-fluoro-1,4-phenylene- or one of the radicals $Q^1$ and $Q^2$ alternatively is trans-1,3-dioxane-2,5-diyl, pyrimidine-2,5-diyl, pyridine-2,5-diyl or 1,4-cyclohexenylene, $R^0$ is n-alkyl, n-alkenyl, n-alkoxy or n-oxaalkyl having in each case up to 9 carbon atoms, Y is H or F and X' is CN, halogen, $CF_3$, $OCF_3$ or $OCHF_2$.

In a further embodiment, the media according to the invention for STN or TN applications are based on compounds of the formula I" in which X' is CN. It should be understood that smaller or greater proportions of other compounds of the formula I" (X'≠CN) are also suitable. For MLC applications, the media according to the invention preferably comprise only up to about 10% by weight of nitrile compounds of the formula I" (but preferably no nitriles of the formula I" but instead of the compounds of the formula I' where X'=halogen, $CF_3$, $OCF_3$ or $OCHF_2$). These media are preferably based on the compounds of the formula II to XII.

The structure of the MLC or STN display according to the invention, comprising polarizers, electrode base-plates and electrodes with surface treatment, corresponds to the construction which is customary for such displays. In this context, the idea of customary construction is very broad and also comprises all variants and modifications of the MLC display, and also, in particular, matrix display elements based on poly-Si TFT or MIM.

A significant difference of the displays according to the invention from those which have been customary up to now, based on the twisted nematic cell, consists, however, in the choice of the liquid-crystal parameters of the liquid-crystal layer.

The liquid-crystal mixtures which can be used in accordance with the invention are prepared in a manner known per se. In general, the desired quantity of the components used in a small quantity is dissolved in the components making up the major constituent, advantageously at elevated temperature. It is also possible to mix solutions of the components in an organic solvent, for example in acetone, chloroform or methanol, and to remove the solvent again after mixing, for example by distillation.

The dielectrics can also comprise other additives which are known to the person skilled in the art and are described in the literature. For example, 0–15% of pleochroic dyes or chiral dopants can be added.

C denotes a crystalline phase, S a smectic phase, $S_c$ a smectic C phase, N a nematic phase and I the isotropic phase.

$V_{10}$ denotes the voltage for 10% transmission (viewed perpendicular to the surface of the plate). $t_{on}$ denotes the switching-on time and $t_{off}$ the switching-off time at an operating voltage corresponding to 2.5 times the value of $V_{10}$. Δn denotes the optical anisotropy and no the refractive index. Δε denotes the dielectric anisotropy (Δε=$ε_1$−$ε_2$, $ε_1$ denoting the dielectric constant parallel to the longitudinal axes of the molecule and $ε_2$ the dielectric constant at right angles thereto). The electrooptical data were measured in a TN cell in the 1st minimum (i.e. at a d~Δn value of 0.5) at 20° C., unless expressly stated otherwise. The optical data were measured at 20° C., unless expressly stated otherwise.

In the present application and in the examples which follow, the structures of the liquid-crystal compounds are indicated by acronyms, the transformation to chemical formulae taking place in accordance Tables A and B below. All radicals $C_nH_{2n+1}$ and $C_mH_{2m+1}$ are straight-chain alkyl radicals having n or m carbon atoms respectively. The coding according to -Table B is self explanatory. In Table A, only the acronym for the parent structure is indicated. In certain cases, the acronym for the parent structure is followed, separated by a hyphen, by a code for the substituents $R^1$, $R^2$, $L^1$ and $L^2$:

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding application German No. P/9505189.0, are hereby incorporated by reference.

| Code for $R^1$ $R^2, L^1, L^2$ | $R^1$ | $R^2$ | $L^1$ | $L^2$ |
|---|---|---|---|---|
| nm | $C_nH_{2n+1}$ | $C_mH_{2m+1}$ | H | H |
| nOm | $C_nH_{2n+1}$ | $OC_mH_{2m+1}$ | H | H |
| nO.m | $OC_nH_{2n+1}$ | $C_mH_{2m+1}$ | H | H |
| n | $C_nH_{2n+1}$ | CN | H | H |
| nN.F | $C_nH_{2n+1}$ | CN | F | H |
| nF | $C_nH_{2n+1}$ | F | H | H |
| nOF | $OC_nH_{2n+1}$ | F | H | H |
| nCl | $C_nH_{2n+1}$ | Cl | H | H |
| nF.F | $C_nH_{2n+1}$ | F | F | H |
| nF.F.F | $C_nH_{2n+1}$ | F | F | F |
| nCF$_3$ | $C_nH_{2n+1}$ | CF$_3$ | H | H |
| nOCF$_3$ | $C_nH_{2n+1}$ | OCF$_3$ | H | H |
| nOCF$_2$ | $C_nH_{2n+1}$ | OCHF$_2$ | H | H |
| nS | $C_nH_{2n+1}$ | NCS | H | H |
| rVsN | $C_rH_{2r+1}$—CH=CH—$C_sH_{2s}$— | CN | H | H |
| rEsN | $C_rH_{2r+1}$—O—$C_sH_{2s}$— | CN | H | H |
| nAm | $C_nH_{2n+1}$ | $COOC_mH_{2m+1}$ | H | H |

The compounds listed in Tables A and B are preferred components in the mixtures according to the invention.

TABLE A:

PYP

PYRP

BCH

TABLE A:-continued

CBC

CCH

CCP

CP

CPTP

CEPTP

D

ECCP

TABLE A:-continued
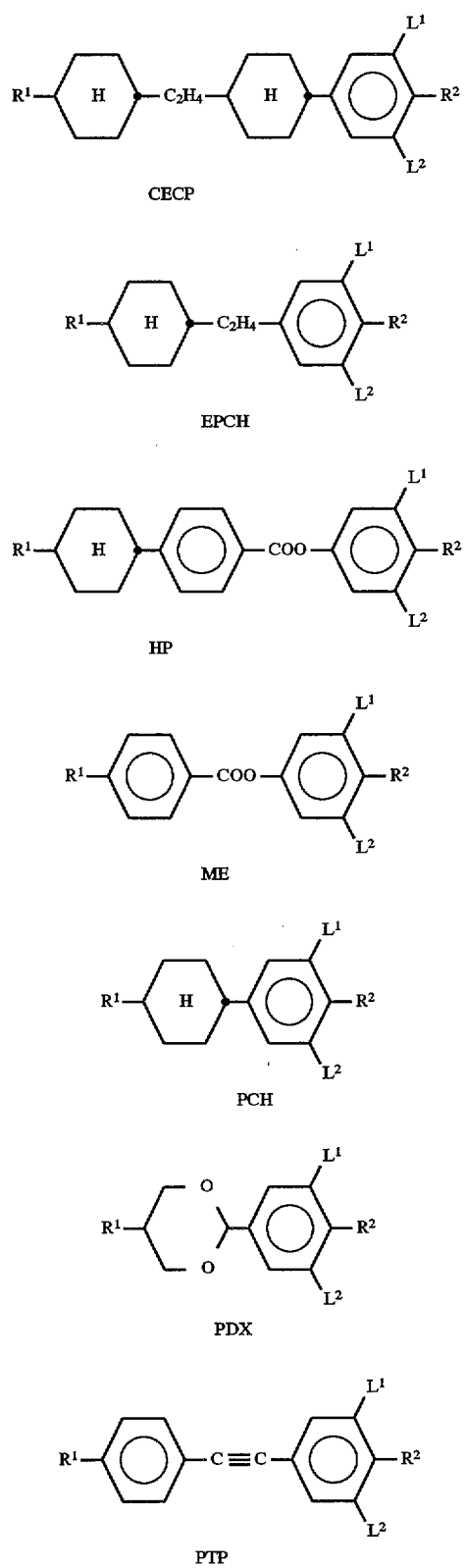
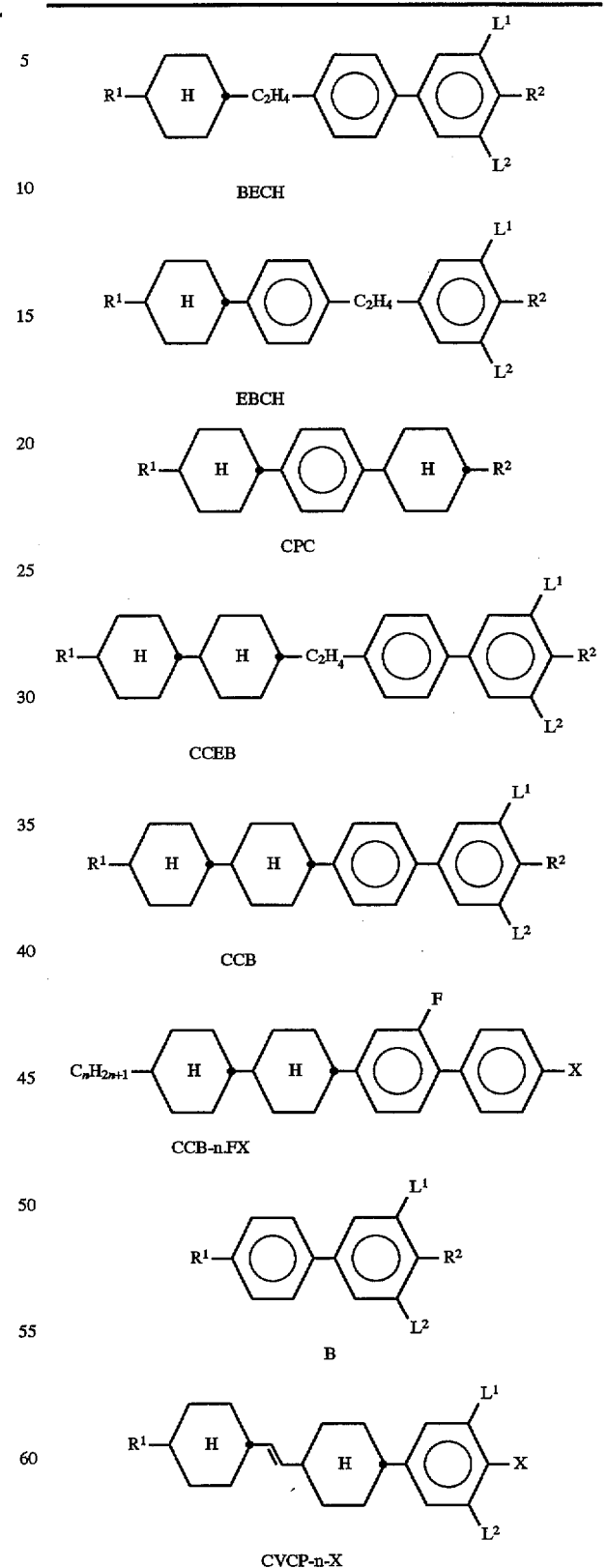

TABLE B
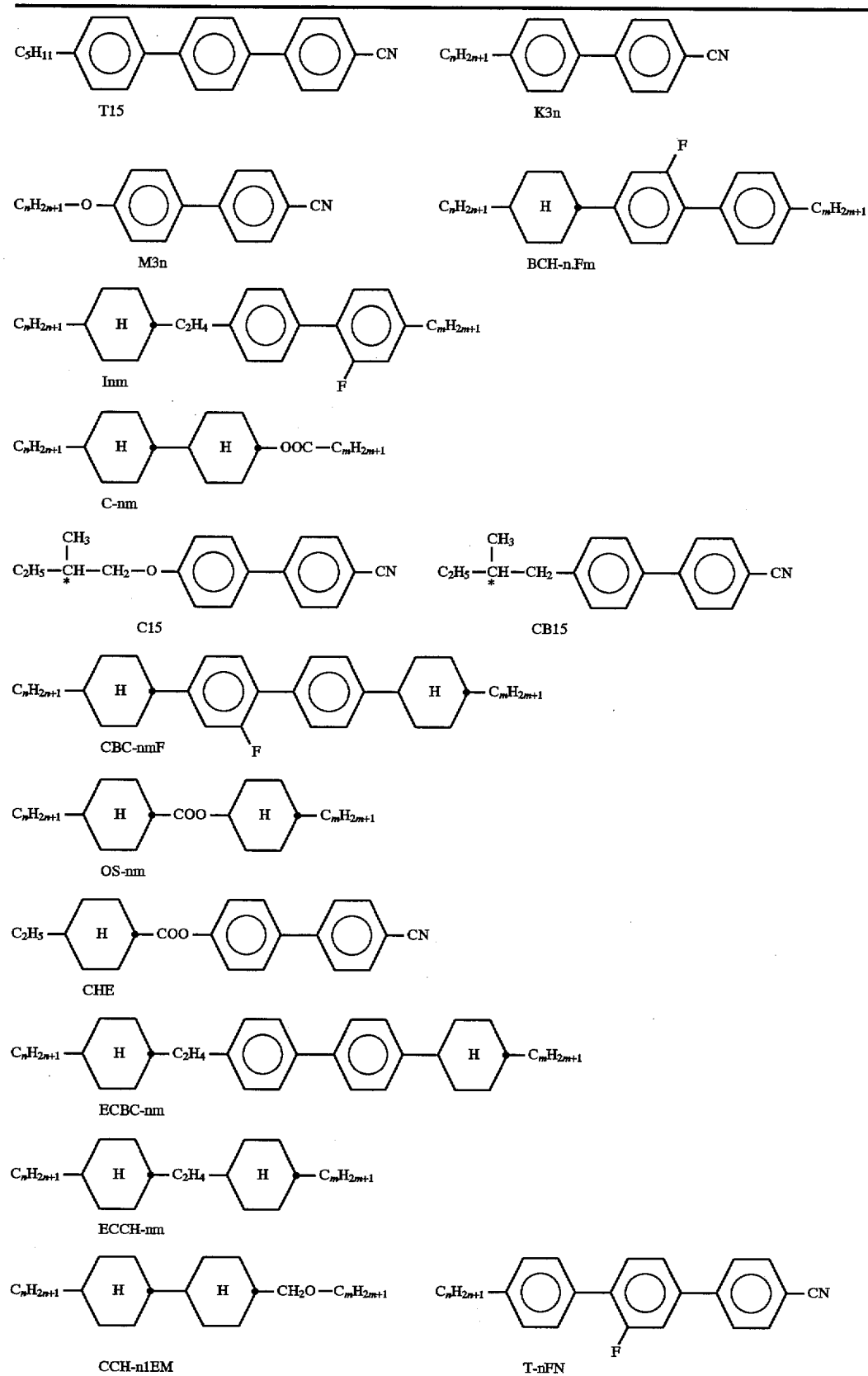

TABLE B-continued

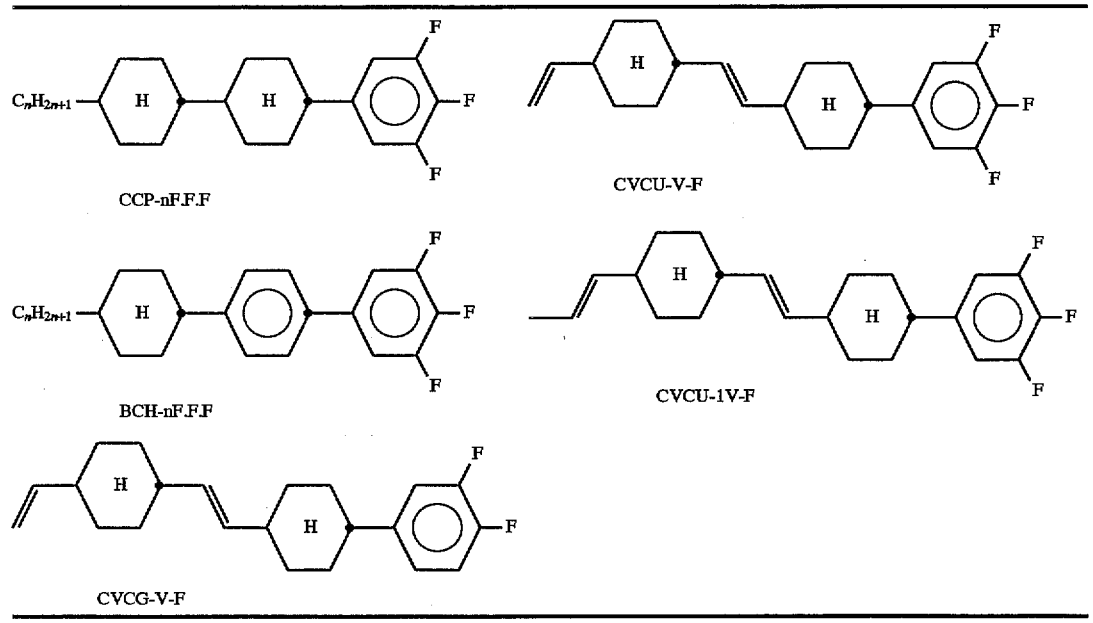

The following examples are intended to illustrate the invention without limiting it. Above and below, percentages are by weight. All temperatures are indicated in degrees Celsius. m.p. denotes melting point, c.p.=clearing point. In addition, K=crystalline state, N=nematic phase, S=smectic phase and I=isotropic phase. The data between these symbols are the transition temperatures. Δn denotes optical anisotropy (589 nm, 20° C.) and the viscosity ($mm^2/sec$) was determined at 20° C.

"Worked up as usual" has the following meaning: water is added if desired, extraction is carried out with dichloromethane, diethyl ether, methyl tert-butyl ether or toluene, the phases are separated, the organic phase is dried and evaporated down, and the product is purified by distillation under reduced pressure or crystallization and/or chromatography. The following abbreviations are used:

BuLi Butyllithium
DAST Diethylaminosulfur trifluoride
DCC Dicyclohexylcarbodiimide
DDQ Dichlorodicyanobenzoquinone
DIBALH Diisobutylaluminum hydride
KOT Potassium tert-butanolate
THF Tetrahydrofuran
pTsOH p-Toluenesulfonic acid
TMEDA Tetramethylethylenediamine

EXAMPLE 1

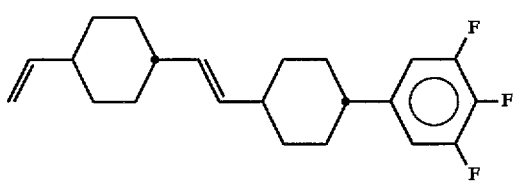

Step 1.1

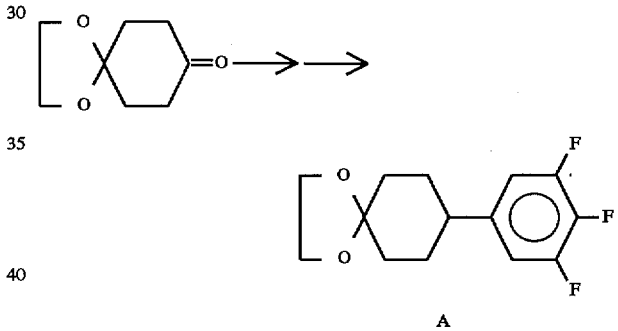

0.15 mol of magnesium are placed in 50 ml of THF under a nitrogen atmosphere, and 0.15 mol of 3,4,5-trifluorobromobenzene in 100 ml of THF is added. The mixture is stirred at room temperature for one hour, and a solution consisting of 0.15 mol of 1,4-cyclohexanedione ethylene ketal in 100 ml of THF is added dropwise to the reaction solution. The mixture is stirred at room temperature for 1 h and then saturated ammonium chloride solution is added. Finally, the mixture is worked up as usual.

The reaction product is dehydrated on a water separator in the heat from boiling with p-toluenesulfonic acid in toluene. The reaction product is then hydrogenated over a Pd/C catalyst.

Step 1.2

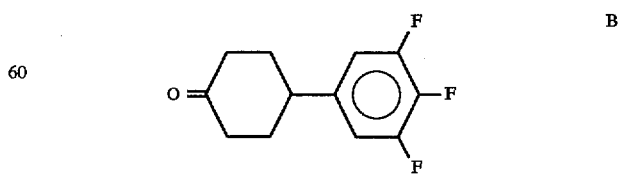

The product from Step 1.1 is dissolved in THF and boiled at reflux in the presence of formic acid for 2 h. Following the addition of water, the mixture is worked up as usual.

Step 1.3

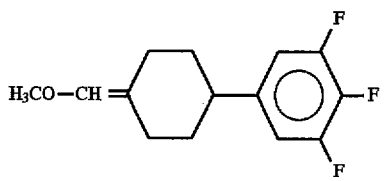
C

In a nitrogen atmosphere, 2.93 mol of methoxy-methyltrimethyltriphenylphosphonium chloride and 2.93 mol of 4-(3,4,5-trifluorophenyl)cyclohexanone from Step 1.2 are dissolved in 4 l of THF, and 2.93 mol of potassium tert-butylate are added with stirring at room temperature. The mixture is stirred for 2 h, water and dilute hydrochloric acid are added, and the mixture is worked up as usual.

Step 1.4

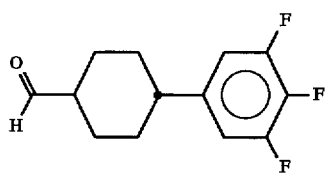
D 50.4 mmol of C, 1.0 g of 10% HCl, 20 ml of THF and 50.4 mmol of acetaldehyde are stirred at room temperature for 0.75 h. Water and methyl tert-butyl ether are added, and the mixture is worked up as usual.

Step 1.5

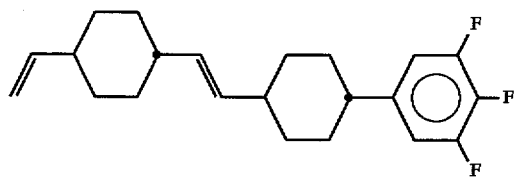
E 0.04 mol of D, 0.04 mol of 4-(trans-4-ethenylcyclohexyl)-methyltriphosphonium iodide and 1140 ml of THF are taken as initial charge, and 0.4 mol of potassium tert-butylate is added in portions, during which the reaction temperature should not exceed 35° C. The mixture is stirred at room temperature overnight, dilute HCl is added and the mixture is worked up as usual. The crude product is dissolved in xylene, iodine is added, and the mixture is boiled at reflux for 15 h. The reaction mixture is allowed to cool, aqueous sodium hydrogen sulfite solution is added, and the mixture is washed with water and concentrated in vacuo. The residue is recrystallized from ethanol.

K 89 N (87.1) I; $\Delta$=0.076; $\Delta\epsilon$=7.09

The following compounds of the formula:

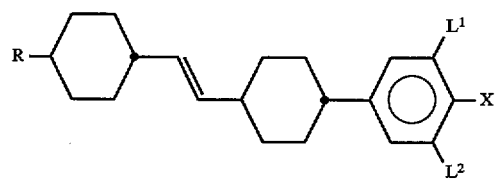

are prepared analogously:

| R | X | L$^1$ | L$^2$ | |
|---|---|---|---|---|
| CH$_2$=CH | F | H | H | K 67 N 152,5 t, $\Delta$n =+0,0097; $\Delta$c =2,33 |
| CH$_2$=CH | F | F | H | K 36 N 118,1 t, $\Delta$n =+0,090; $\Delta$c =4,54 |
| CH$_3$-CH=CH | F | F | H | |
| CH$_3$-CH=CH | F | F | F | |
| CH$_3$-CH=CH | F | H | H | |
| CH$_3$-CH=CH-CH$_2$ | F | F | H | |
| CH$_3$-CH=CH-CH$_2$ | F | F | F | |
| CH$_3$-CH$_2$-CH=CH | F | F | H | |
| CH$_3$-CH$_2$-CH=CH | F | F | F | |
| CH$_3$-CH=CH-CH$_2$ | F | F | H | |
| CH$_3$-CH=CH-CH$_2$ | F | F | F | |
| CH$_3$-CH$_2$-CH$_2$-CH=CH | F | F | H | |
| CH$_3$-CH$_2$-CH$_2$-CH=CH | F | F | F | |
| CH$_3$-CH$_2$-CH=CH-CH$_2$ | F | F | H | |
| CH$_3$-CH$_2$-CH=CH-CH$_2$ | F | F | F | |
| CH$_3$-CH=CH-CH$_2$CH$_2$ | F | F | H | |
| CH$_3$-CH=CH-CH$_2$-CH$_2$ | F | F | F | |
| CH$_2$=CH-CH$_2$ | F | F | H | |
| CH$_2$=CH-CH$_2$ | F | F | F | |
| CH$_2$=CH-CH$_2$-CH$_2$ | F | F | H | |
| CH$_2$=CH-CH$_2$-CH$_2$ | F | F | F | |
| CH$_2$=CH-CH$_2$-CH$_2$ | F | H | H | |
| CH$_2$=CH | Cl | F | H | |
| CH$_2$=CH | Cl | F | F | |
| CH$_3$-CH=CH | Cl | F | H | |
| CH$_3$-CH=CH | Cl | F | F | |

-continued

| R | X | L¹ | L² |
|---|---|---|---|
| CH₃—CH=CH—CH₂ | Cl | F | H |
| CH₃—CH=CH—CH₂ | Cl | F | F |
| CH₃—CH₂—CH=CH | Cl | F | H |
| CH₃—CH₂—CH=CH | Cl | F | F |
| CH₃—CH=CH—CH₂ | Cl | F | H |
| CH₃—CH=CH—CH₂ | Cl | F | F |
| CH₃—CH₂—CH₂—CH=CH | Cl | F | H |
| CH₃—CH₂—CH₂—CH=CH | Cl | F | F |
| CH₃—CH₂—CH=CH—CH₂ | Cl | F | H |
| CH₃—CH₂—CH=CH—CH₂ | Cl | F | F |
| CH₃—CH=CH—CH₂—CH₂ | Cl | F | H |
| CH₃—CH=CH—CH₂—CH₂ | Cl | F | F |
| CH₂—CH=CH₂ | Cl | F | H |
| CH₂—CH=CH₂ | Cl | F | F |
| CH₂=CH—CH₂—CH₂ | Cl | F | H |
| CH₂=CH—CH₂—CH₂ | Cl | F | F |
| CH₂=CH—CH₂—CH₂ | Cl | H | H |
| CH₂=CH | OCF₃ | F | H |
| CH₂=CH | OCF₃ | F | F |
| CH₃—CH=CH | OCF₃ | F | H |
| CH₃—CH=CH | OCF₃ | F | F |
| CH₃—CH=CH—CH₂ | OCF₃ | F | H |
| CH₃—CH=CH—CH₂ | OCF₃ | F | F |
| CH₃—CH₂—CH=CH | OCF₃ | F | H |
| CH₃—CH₂—CH=CH | OCF₃ | F | F |
| CH₃—CH=CH—CH₂ | OCF₃ | F | H |
| CH₃—CH=CH—CH₂ | OCF₃ | F | F |
| CH₃—CH₂—CH₂—CH=CH | OCF₃ | F | H |
| CH₃—CH₂—CH₂—CH=CH | OCF₃ | F | F |
| CH₃—CH₂—CH=CH—CH₂ | OCF₃ | F | H |
| CH₃—CH₂—CH=CH—CH₂ | OCF₃ | F | F |
| CH₃—CH=CH—CH₂—CH₂ | OCF₃ | F | H |
| CH₃—CH=CH—CH₂—CH₂ | OCF₃ | F | F |
| CH₃—CH=CH—CH₂—CH₂ | OCF₃ | H | H |
| CH₂—CH=CH₂ | OCF₃ | F | H |
| CH₂—CH=CH₂ | OCF₃ | F | F |
| CH₂=CH—CH₂—CH₂ | OCF₃ | F | H |
| CH₂=CH—CH₂—CH₂ | OCF₃ | F | F |
| CH₂=CH—CH₂—CH₂ | OCF₃ | H | H |
| CH₂=CH | OCHF₂ | F | H |
| CH₂=CH | OCHF₂ | F | F |
| CH₂=CH | OCHF₂ | H | H |
| CH₃—CH=CH | OCHF₂ | F | H |
| CH₃—CH=CH | OCHF₂ | F | F |
| CH₃—CH=CH—CH₂ | OCHF₂ | F | H |
| CH₃—CH=CH—CH₂ | OCHF₂ | F | F |
| CH₃—CH₂—CH=CH | OCHF₂ | F | H |
| CH₃—CH₂—CH=CH | OCHF₂ | F | F |
| CH₃—CH=CH—CH₂ | OCHF₂ | F | H |
| CH₃—CH=CH—CH₂ | OCHF₂ | F | F |
| CH₃—CH₂—CH₂—CH=CH | OCHF₂ | F | H |
| CH₃—CH₂—CH₂—CH=CH | OCHF₂ | F | F |
| CH₃—CH₂—CH=CH—CH₂ | OCHF₂ | F | H |
| CH₃—CH₂—CH=CH—CH₂ | OCHF₂ | F | F |
| CH₃—CH=CH—CH₂—CH₂ | OCHF₂ | F | H |
| CH₃—CH=CH—CH₂—CH₂ | OCHF₂ | F | F |
| CH₂—CH=CH₂ | OCHF₂ | F | H |
| CH₂—CH=CH₂ | OCHF₂ | F | F |
| CH₂=CH—CH₂—CH₂ | OCHF₂ | F | H |
| CH₂=CH—CH₂—CH₂ | OCHF₂ | F | F |
| CH₂=CH—CH₂—CH₂ | OCHF₂ | H | H |
| CH₂=CH | OCH₂CF₃ | F | H |
| CH₂=CH | OCH₂CF₃ | F | F |
| CH₃—CH=CH | OCH₂CF₃ | F | H |
| CH₃—CH=CH | OCH₂CF₃ | F | F |
| CH₃—CH=CH—CH₂ | OCH₂CF₃ | F | H |
| CH₃—CH=CH—CH₂ | OCH₂CF₃ | F | F |
| CH₃—CH₂—CH=CH | OCH₂CF₃ | F | H |
| CH₃—CH₂—CH=CH | OCH₂CF₃ | F | F |
| CH₃—CH₂—CH=CH | OCH₂CF₃ | H | H |
| CH₃—CH=CH—CH₂ | OCH₂CF₃ | F | H |
| CH₃—CH=CH—CH₂ | OCH₂CF₃ | F | F |
| CH₃—CH₂—CH₂—CH=CH | OCH₂CF₃ | F | H |
| CH₃—CH₂—CH₂—CH=CH | OCH₂CF₃ | F | F |
| CH₃—CH₂—CH=CH—CH₂ | OCH₂CF₃ | F | H |
| CH₃—CH₂—CH=CH—CH₂ | OCH₂CF₃ | F | F |
| CH₃—CH=CH—CH₂—CH₂ | OCH₂CF₃ | F | H |
| CH₃—CH=CH—CH₂—CH₂ | OCH₂CF₃ | F | F |

-continued

| R | X | L¹ | L² |
|---|---|----|----|
| CH₂—CH=CH₂ | OCH₂CF₃ | F | H |
| CH₂—CH=CH₂ | OCH₂CF₃ | F | F |
| CH₂=CH—CH₂—CH₂ | OCH₂CF₃ | F | H |
| CH₂=CH—CH₂—CH₂ | OCH₂CF₃ | F | F |
| CH₂=CH—CH₂—CH₂ | OCH₂CF₃ | H | H |
| CH₂=CH | OCHFCF₃ | F | H |
| CH₂=CH | OCHFCF₃ | F | F |
| CH₂=CH | OCHFCF₃ | H | H |
| CH₃—CH=CH | OCHFCF₃ | F | H |
| CH₃—CH=CH | OCHFCF₃ | F | F |
| CH₃—CH=CH—CH₂ | OCHFCF₃ | F | H |
| CH₃—CH=CH—CH₂ | OCHFCF₃ | F | F |
| CH₃—CH₂—CH=CH | OCHFCF₃ | F | H |
| CH₃—CH₂—CH=CH | OCHFCF₃ | F | F |
| CH₃—CH=CH—CH₂ | OCHFCF₃ | F | H |
| CH₃—CH=CH—CH₂ | OCHFCF₃ | F | F |
| CH₃—CH₂—CH₂—CH=CH | OCHFCF₃ | F | H |
| CH₃—CH₂—CH₂—CH=CH | OCHFCF₃ | F | F |
| CH₃—CH₂—CH=CH—CH₂ | OCHFCF₃ | F | H |
| CH₃—CH₂—CH=CH—CH₂ | OCHFCF₃ | F | F |
| CH₃—CH=CH—CH₂—CH₂ | OCHFCF₃ | F | H |
| CH₃—CH=CH—CH₂—CH₂ | OCHFCF₃ | F | F |
| CH₂—CH—CH=CH₂ | OCHFCF₃ | F | H |
| CH₂—CH—CH=CH₂ | OCHFCF₃ | F | F |
| CH₂=CH—CH₂—CH₂ | OCHFCF₃ | H | H |
| CH₂=CH—CH₂—CH₂ | OCH₂CHF₂ | F | H |
| CH₂=CH—CH₂—CH₂ | OCH₂CHF₂ | F | H |
| CH₂=CH | OCH₂CHF₂ | F | H |
| CH₂=CH | OCH₂CHF₂ | F | F |
| CH₃—CH=CH | OCH₂CHF₂ | F | H |
| CH₃—CH=CH | OCH₂CHF₂ | F | F |
| CH₃—CH=CH—CH₂ | OCH₂CHF₂ | F | H |
| CH₃—CH=CH—CH₂ | OCH₂CHF₂ | F | F |
| CH₃—CH₂—CH=CH | OCH₂CHF₂ | F | H |
| CH₃—CH₂—CH=CH | OCH₂CHF₂ | F | F |
| CH₃—CH=CH—CH₂ | OCH₂CHF₂ | F | H |
| CH₃—CH=CH—CH₂ | OCH₂CHF₂ | F | F |
| CH₃—CH₂—CH₂—CH=CH | OCH₂CHF₂ | F | H |
| CH₃—CH₂—CH₂—CH=CH | OCH₂CHF₂ | F | F |
| CH₃—CH₂—CH=CH—CH₂ | OCH₂CHF₂ | F | H |
| CH₃—CH₂—CH=CH—CH₂ | OCH₂CHF₂ | F | F |
| CH₃—CH=CH—CH₂—CH₂ | OCH₂CHF₂ | F | H |
| CH₃—CH=CH—CH₂—CH₂ | OCH₂CHF₂ | F | F |
| CH₂—CH=CH₂ | OCH₂CHF₂ | F | H |
| CH₂—CH=CH₂ | OCH₂CHF₂ | F | F |
| CH₂=CH—CH₂—CH₂ | OCH₂CHF₂ | F | H |
| CH₂=CH—CH₂—CH₂ | OCH₂CHF₂ | F | F |
| CH₂=CH—CH₂—CH₂ | OCH₂CHF₂ | H | H |
| CH₂=CH | OC₂F₅ | F | H |
| CH₂=CH | OC₂F₅ | F | F |
| CH₃—CH=CH | OC₂F₅ | F | H |
| CH₃—CH=CH | OC₂F₅ | F | F |
| CH₃—CH=CH—CH₂ | OC₂F₅ | F | H |
| CH₃—CH=CH—CH₂ | OC₂F₅ | F | F |
| CH₃—CH₂—CH=CH | OC₂F₅ | F | H |
| CH₃—CH₂—CH=CH | OC₂F₅ | F | F |
| CH₃—CH=CH—CH₂ | OC₂F₅ | F | H |
| CH₃—CH=CH—CH₂ | OC₂F₅ | F | F |
| CH₃—CH₂—CH₂—CH=CH | OC₂F₅ | F | H |
| CH₃—CH₂—CH₂—CH=CH | OC₂F₅ | F | F |
| CH₃—CH₂—CH₂—CH=CH | OC₂F₅ | H | H |
| CH₃—CH₂—CH=CH—CH₂ | OC₂F₅ | F | H |
| CH₃—CH₂—CH=CH—CH₂ | OC₂F₅ | F | F |
| CH₃—CH₂—CH=CH—CH₂ | OC₂F₅ | H | H |
| CH₃—CH=CH—CH₂—CH₂ | OC₂F₅ | F | F |
| CH₃—CH=CH—CH₂—CH₂ | OC₂F₅ | H | H |
| CH₂—CH=CH₂ | OC₂F₅ | F | F |
| CH₂—CH=CH₂ | OC₂F₅ | F | H |
| CH₂=CH—CH₂—CH₂ | OC₂F₅ | F | F |
| CH₂=CH—CH₂—CH₂ | OC₂F₅ | F | H |
| CH₂=CH—CH₂—CH₂ | OC₂F₅ | H | H |
| CH₂=CH | OC₃F₇ | F | H |
| CH₂=CH | OC₃F₇ | F | F |
| CH₃—CH=CH | OC₃F₇ | F | H |
| CH₃—CH=CH | OC₃F₇ | F | F |
| CH₃—CH=CH—CH₂ | OC₃F₇ | F | H |
| CH₃—CH=CH—CH₂ | OC₃F₇ | F | F |
| CH₃—CH₂—CH=CH | OC₃F₇ | F | H |

-continued

| R | X | L¹ | L² |
|---|---|----|----|
| CH₃—CH₂—CH=CH | OC₃F₇ | F | F |
| CH₃—CH=CH—CH₂ | OC₃F₇, | F | H |
| CH₃—CH=CH—CH₂ | OC₃F₇ | F | F |
| CH₃—CH₂—CH₂—CH=CH | OC₃F₇ | F | H |
| CH₃—CH₂—CH₂—CH=CH | OC₃F₇ | F | F |
| CH₃—CH₂—CH=CH—CH₂ | OC₃F₇ | F | H |
| CH₃—CH₂—CH=CH—CH₂ | OC₃F₇ | F | F |
| CH₃—CH=CH—CH₂—CH₂ | OC₃F₇ | F | H |
| CH₃—CH=CH—CH₂—CH₂ | OC₃F₇ | F | F |
| CH₂—CH=CH₂ | OC₃F₇ | F | H |
| CH₂—CH=CH₂ | OC₃F₇ | F | F |
| CH₂=CH—CH₂—CH₂ | OC₃F₇ | F | H |
| CH₂=CH—CH₂—CH₂ | OC₃F₇ | F | F |
| CH₂=CH—CH₂—CH₂ | OC₃F₇ | H | H |
| CH₂=CH | OCH₂CHF₂ | F | H |
| CH₂=CH | OCH₂CHF₂ | F | F |
| CH₃—CH=CH | OCH₂CHF₂ | F | H |
| CH₃—CH=CH | OCH₂CHF₂ | F | F |
| CH₃—CH=CH | OCH₂CHF₂ | H | H |
| CH₃—CH=CH—CH₂ | OCH₂CHF₂ | F | H |
| CH₃—CH=CH—CH₂ | OCH₂CHF₂ | F | F |
| CH₃—CH₂—CH=CH | OCH₂CHF₂ | F | H |
| CH₃—CH₂—CH=CH | OCH₂CHF₂ | F | F |
| CH₃—CH=CH—CH₂ | OCH₂F₂ | F | H |
| CH₃—CH=CH—CH₂ | OCH₂F₂ | F | F |
| CH₃—CH₂—CH₂—CH=CH | OCH₂CHF₂ | F | H |
| CH₃—CH₂—CH₂—CH=CH | OCH₂CHF₂ | F | F |
| CH₃—CH₂—CH=CH—CH₂ | OCH₂CHF₂ | F | H |
| CH₃—CH₂—CH=CH—CH₂ | OCH₂CHF₂ | F | F |
| CH₃—CH=CH—CH₂—CH₂ | OCH₂CHF₂ | F | H |
| CH₃—CH=CH—CH₂—CH₂ | OCH₂CHF₂ | F | F |
| CH₂—CH=CH₂ | OCH₂CHF₂ | F | H |
| CH₂—CH=CH₂ | OCH₂CHF₂ | F | F |
| CH₂=CH—CH₂—CH₂ | OCH₂CHF₂ | F | H |
| CH₂=CH—CH₂—CH₂ | OCH₂CHF₂ | F | F |
| CH₂=CH—CH₂—CH₂ | OCH₂CHF₂ | H | H |
| CH₂=CH | OCHFCF₂CF₃ | F | H |
| CH₂=CH | OCHFCF₂CF₃ | F | F |
| CH₃—CH=CH | OCHFCF₂CF₃ | F | H |
| CH₃—CH=CH | OCHFCF₂CF₃ | F | F |
| CH₃—CH=CH—CH₂ | OCHFCF₂CF₃ | F | H |
| CH₃—CH=CH—CH₂ | OCHFCF₂CF₃ | F | F |
| CH₃—CH₂—CH=CH | OCHFCF₂CF₃ | F | H |
| CH₃—CH₂=CH=CH | OCHFCF₂CF₃ | F | F |
| CH₃—CH=CH—CH₂ | OCHFCF₂CF₃ | F | H |
| CH₃—CH=CH—CH₂ | OCHFCF₂CF₃ | F | F |
| CH₃—CH₂—CH₂—CH=CH | OCHFCF₂CF₃ | F | H |
| CH₃—CH₂—CH₂—CH=CH | OCHFCF₂CF₃ | F | F |
| CH₃—CH₂—CH=CH—CH₂ | OCHFCF₂CF₃ | F | H |
| CH₃—CH₂—CH=CH—CH₂ | OCHFCF₂CF₃ | F | F |
| CH₃—CH=CH—CH₂—CH₂ | OCHFCF₂CF₃ | F | H |
| CH₃—CH=CH—CH₂—CH₂ | OCHFCF₂CF₃ | F | F |
| CH₃—CH=CH—CH₂—CH₂ | OCHFCF₂CF₃ | H | H |
| CH₂—CH=CH₂ | OCHFCF₂CF₃ | F | H |
| CH₂—CH=CH₂ | OCHFCF₂CF₃ | F | F |
| CH₂=CH—CH₂—CH₂ | OCHFCF₂CF₃ | F | H |
| CH₂=CH—CH₂—CH₂ | OCHFCF₂CF₃ | F | F |
| CH₂=CH—CH₂—CH₂ | OCHFCF₂CF₃ | H | H |
| CH₂=CH | OCF₂CHFCF₃ | F | H |
| CH₂=CH | OCF₂CHFCF₃ | F | F |
| CH₃—CH=CH | OCF₂CHFCF₃ | F | H |
| CH₃—CH=CH | OCF₂CHFCF₃ | F | F |
| CH₃—CH=CH—CH₂ | OCF₂CHFCF₃ | F | H |
| CH₃—CH=CH—CH₂ | OCF₂CHFCF₃ | F | F |
| CH₃—CH₂—CH=CH | OCF₂CHFCF₃ | F | H |
| CH₃—CH₂—CH=CH | OCF₂CHFCF₃ | F | F |
| CH₃—CH=CH—CH₂ | OCF₂CHFCF₃ | F | H |
| CH₃—CH=CH—CH₂ | OCF₂CHFCF₃ | F | F |
| CH₃—CH₂—CH₂CH=CH | OCF₂CHFCF₃ | F | H |
| CH₃—CH₂—CH₂CH=CH | OCF₂CHFCF₃ | F | F |
| CH₃—CH₂—CH=CH—CH₂ | OCF₂CHFCF₃ | F | H |
| CH₃—CH₂—CH=CH—CH₂ | OCF₂CHFCF₃ | F | F |
| CH₃—CH=CH—CH₂—CH₂ | OCF₂CHFCF₃ | F | H |
| CH₃—CH=CH—CH₂—CH₂ | OCF₂CHFCF₃ | F | F |
| CH₂—CH=CH₂ | OCF₂CHFCF₃ | F | H |
| CH₂—CH=CH₂ | OCF₂CHFCF₃ | F | F |
| CH₂=CH—CH₂—CH₂ | OCF₂CHFCF₃ | F | H |
| CH₂=CH—CH₂—CH₂ | OCF₂CHFCF₃ | F | F |

-continued

| R | X | L¹ | L² |
|---|---|---|---|
| CH₂=CH—CH₂—CH₂ | OCF₂CHFCF₃ | H | H |
| CH₂=CH | COCF₃ | F | H |
| CH₂=CH | COCF₃ | F | F |
| CH₃—CH=CH | COCF₃ | F | H |
| CH₃—CH=CH | COCF₃ | F | F |
| CH₃—CH=CH—CH₂ | COCF₃ | F | H |
| CH₃—CH=CH—CH₂ | COCF₃ | F | F |
| CH₃—CH₂—CH=CH | COCF₃ | F | H |
| CH₃—CH₂—CH=CH | COCF₃ | F | F |
| CH₃—CH₂—CH=CH | COCF₃ | H | H |
| CH₃—CH=CH—CH₂ | COCF₃ | F | H |
| CH₃—CH=CH—CH₂ | COCF₃ | F | F |
| CH₃—CH₂—CH₂—CH=CH | COCF₃ | F | H |
| CH₃—CH₂—CH₂—CH=CH | COCF₃ | F | F |
| CH₃—CH₂—CH=CH—CH₂ | COCF₃ | F | H |
| CH₃—CH₂—CH=CH—CH₂ | COCF₃ | F | F |
| CH₃—CH=CH—CH₂—CH₂ | COCF₃ | F | H |
| CH₃—CH=CH—CH₂—CH₂ | COCF₃ | F | F |
| CH₂—CH=CH₂ | COCF₃ | F | H |
| CH₂—CH=CH₂ | COCF₃ | F | F |
| CH₂=CH—CH₂—CH₂ | COCF₃ | F | H |
| CH₂=CH—CH₂—CH₂ | COCF₃ | F | F |
| CH₂=CH—CH₂—CH₂ | COCF₃ | H | H |
| CH₂=CH | OCHFCHF₂ | F | H |
| CH₂=CH | OCHFCHF₂ | F | F |
| CH₃—CH=CH | OCHFCHF₂ | F | H |
| CH₃—CH=CH | OCHFCHF₂ | F | F |
| CH₃—CH=CH—CH₂ | OCHFCHF₂ | F | H |
| CH₃—CH=CH—CH₂ | OCHFCHF₂ | F | F |
| CH₃—CH₂—CH=CH | OCHFCHF₂ | F | H |
| CH₃—CH₂—CH=CH | OCHFCHF₂ | F | F |
| CH₃—CH=CH—CH₂ | OCHFCHF₂ | F | H |
| CH₃—CH=CH—CH₂ | OCHFCHF₂ | F | F |
| CH₃—CH₂—CH₂—CH=CH | OCHFCHF₂ | F | H |
| CH₃—CH₂—CH₂—CH=CH | OCHFCHF₂ | F | F |
| CH₃—CH₂—CH=CH—CH₂ | OCHFCHF₂ | F | H |
| CH₃—CH₂—CH=CH—CH₂ | OCHFCHF₂ | F | F |
| CH₃—CH=CH—CH₂—CH₂ | OCHFCHF₂ | F | H |
| CH₃—CH=CH—CH₂—CH₂ | OCHFCHF₂ | F | F |
| CH₂—CH=CH₂ | OCHFCHF₂ | F | H |
| CH₂—CH=CH₂ | OCHFCHF₂ | F | F |
| CH₂=CH—CH₂—CH₂ | OCHFCHF₂ | F | H |
| CH₂=CH—CH₂—CH₂ | OCHFCHF₂ | F | F |
| CH₂=CH—CH₂—CH₂ | OCHFCHF₂ | H | H |

MIXTURE EXAMPLES

Example 1

| | | | |
|---|---|---|---|
| PCH-5F | 5.0% | Clearing point [°C.]: | 92 |
| PCH-7F | 6.0% | V₍₁₀,₀,₂₀₎: | 1.35 V |
| CCP-20CF₃ | 11.0% | | |
| CCP-30CF₃ | 12.0% | | |
| CCP-40CF₃ | 10.0% | | |
| CCP-50CF₃ | 12.0% | | |
| BCH-3F.F | 12.0% | | |
| BCH-5F.F | 11.0% | | |
| CVCU-V-F | 21.0% | | |

Example 2

| | | | |
|---|---|---|---|
| PCH-5F | 5.0% | Clearing point [°C.]: | 93 |
| PCH-7F | 6.0% | V₍₁₀,₀,₂₀₎: | 1.38 V |
| CCP-20CF₃ | 11.0% | | |
| CCP-30CF₃ | 12.0% | | |
| CCP-40CF₃ | 10.0% | | |
| CCP-50CF₃ | 12.0% | | |
| BCH-3F.F | 12.0% | | |

-continued

| | | | |
|---|---|---|---|
| BCH-5F.F | 11.0% | | |
| CVCU-1V-F | 21.0% | | |

Example 3

| | | | |
|---|---|---|---|
| PCH-5F | 9.0% | Clearing point [°C.]: | 96 |
| PCH-6F | 7.2% | V₍₁₀,₀,₂₀₎: | 1.84 V |
| PCH-7F | 5.4% | | |
| CCP-20CF₃ | 7.2% | | |
| CCP-30CF₃ | 10.8% | | |
| CCP-40CF₃ | 8.1% | | |
| CCP-50CF₃ | 8.1% | | |
| BCH-3F.F | 10.8% | | |
| BCH-5F.F | 9.0% | | |
| ECCP-30CF₃ | 4.5% | | |
| ECCP-50CF₃ | 4.5% | | |
| CBC-33F | 1.8% | | |
| CBC-53F | 1.8% | | |
| CBC-55F | 1.8% | | |
| CVCU-1V-F | 10.0% | | |

Example 4

| | | | |
|---|---|---|---|
| PCH-5F | 4.5% | Clearing point [°C.]: | 97 |
| PCH-7F | 5.4% | $V_{(10,0,20)}$: | 1.25 V |
| CCP-20CF$_3$ | 10.0% | | |
| CCP-30CF$_3$ | 11.0% | | |
| CCP-40CF$_3$ | 9.0% | | |
| CCP-50CF$_3$ | 11.0% | | |
| BCH-3F.F | 11.0% | | |
| BCH-5F.F | 10.0% | | |
| CCP-3F.F | 11.0% | | |
| CCP-5F.F | 8.1% | | |
| CVCU-V-F | 9.0% | | |

Example 5

| | | | |
|---|---|---|---|
| PCH-5F | 9.0% | Clearing point [°C.]: | 98.2 |
| PCH-6F | 7.2% | Δn [589 nm, 20° C.]: | 0.0973 |
| PCH-7F | 5.4% | Δε [1 kHz, 20° C.]: | 5.48 |
| CCP-20CF$_3$ | 7.2% | | |
| CCP-30CF$_3$ | 10.8% | | |
| CCP-40CF$_3$ | 8.1% | | |
| CCP-50CF$_3$ | 8.1% | | |
| BCH-3.F | 10.8% | | |
| BCH-5.F | 9.0% | | |
| ECCP-30CF$_3$ | 4.5% | | |
| ECCP-50CF$_3$ | 4.5% | | |
| CBC-33F | 1.8% | | |
| CBC-53F | 1.8% | | |
| CBC-55F | 1.8% | | |
| CVCP-V-F | 10.0% | | |

Example 6

| | | | |
|---|---|---|---|
| PCH-5F | 9.0% | Clearing point [°C.]: | 94.3 |
| PCH-6F | 7.2% | Δn [589 nm, 20° C.]: | 0.0966 |
| PCH-7F | 5.4% | ν [mm$^2$ · s$^{-1}$, 20° C.]: | 14 |
| CCP-20CF$_3$ | 7.2% | Δε [1 kHz, 20° C.]: | 5.83 |
| CCP-30CF$_3$ | 10.8% | | |
| CCP-40CF$_3$ | 8.1% | | |
| CCP-50CF$_3$ | 8.1% | | |
| BCH-3F.F | 10.8% | | |
| BCH-5F.F | 9.0% | | |
| ECCP-30CF$_3$ | 4.5% | | |
| ECCP-50CF$_3$ | 4.5% | | |
| CBC-33F | 1.8% | | |
| CBC-53F | 1.8% | | |
| CBC-55F | 1.8% | | |
| CVCP-V-F | 10.0% | | |

Example 7

| | | | |
|---|---|---|---|
| PCH-5F | 9.0% | Clearing point [°C.]: | 90.6 |
| PCH-6F | 7.2% | Δn [589 nm, 20° C.]: | 0.0952 |
| PCH-7F | 5.4% | ν [mm$^2$ · s$^{-1}$, 20° C.]: | 15 |
| CCP-20CF$_3$ | 7.2% | Δε [1 kHz, 20° C.]: | 6.18 |
| CCP-30CF$_3$ | 10.8% | | |
| CCP-40CF$_3$ | 8.1% | | |
| CCP-50CF$_3$ | 8.1% | | |
| BCH-3F.F | 10.8% | | |
| BCH-5F.F | 9.0% | | |
| ECCP-30CF$_3$ | 4.5% | | |
| ECCP-50CF$_3$ | 4.5% | | |
| CBC-33F | 1.8% | | |
| CBC-53F | 1.8% | | |
| CBC-55F | 1.8% | | |
| CVCP-V-F | 10.0% | | |

Example 8

| | | | |
|---|---|---|---|
| PCH-5F | 3.20% | Clearing point [°C.]: | +116 |
| CCP-20CF$_2$.F.F | 17.04% | Δε [1 kHz, 20° C.]: | +8.1 |
| CCP-30CF$_2$.F.F | 16.00% | | |
| CCP-50CF$_2$.F.F | 17.04% | | |
| CUP-2F.F | 5.36% | | |
| CUP-3F.F | 5.36% | | |
| CBC-33F | 5.36% | | |
| CBC-53F | 5.36% | | |
| CBC-55F | 5.28% | | |
| CVCU-V-F | 20.00% | | |

Example 9

| | | | |
|---|---|---|---|
| PCH-5F | 3.20% | Clearing point [°C.]: | +122 |
| CCP-20CF$_2$.F.F | 17.04% | Δε [1 kHz, 20° C.]: | +7.3 |
| CCP-30CF$_2$.F.F | 16.00% | | |
| CCP-50CF$_2$.F.F | 17.04% | | |
| CUP-2F.F | 5.36% | | |
| CUP-3F.F | 5.36% | | |
| CBC-33F | 5.36% | | |
| CBC-53F | 5.36% | | |
| CBC-55F | 5.28% | | |
| CVCU-V-F | 20.00% | | |

Example 10

| | | | |
|---|---|---|---|
| PCH-3 | 20.00% | Clearing point [°C.]: | 103.3 |
| K6 | 6.40% | Δε (1 kHz, 20° C.]: | +9.8 |
| K9 | 7.20% | $V_{(10,0,20)}$ [V]: | 1.18 |
| CCP-20CF$_3$ | 4.00% | | |
| CCP-30CF$_3$ | 4.00% | | |
| CCP-40CF$_3$ | 4.00% | | |
| CCP-50CF$_3$ | 4.00% | | |
| ECCP-20CF$_3$ | 4.00% | | |
| ECCP-30CF$_3$ | 4.00% | | |
| ECCP-50CF$_3$ | 4.00% | | |
| ECCP-3F | 4.00% | | |
| ECCP-5F | 4.00% | | |
| CBC-33F | 4.00% | | |
| CBC-53F | 3.20% | | |
| CBC-55F | 3.20% | | |
| CVCG-V-F | 20.00% | | |

Example 11

| | | | |
|---|---|---|---|
| PCH-3 | 20.00% | Clearing point [°C.]: | 99.5 |
| KG | 6.40% | Δε (1 kHz, 20° C.]: | +10.7 |
| K9 | 7.20% | $V_{(10,0,20)}$ [V] | 1.18 |
| CCP-20CF$_3$ | 4.00% | | |
| CCP-30CF$_3$ | 4.00% | | |
| CCP-40CF$_3$ | 4.00% | | |
| CCP-50CF$_3$ | 4.00% | | |
| ECCP-20CF$_3$ | 4.00% | | |
| ECCP-30CF$_3$ | 4.00% | | |
| ECCP-50CF$_3$ | 4.00% | | |
| ECCP-3F | 4.00% | | |
| ECCP-5F | 4.00% | | |
| CBC-33F | 4.00% | | |
| CBC-53F | 3.20% | | |
| CBC-55F | 3.20% | | |
| CVCG-V-F | 20.00% | | |

We claim:
1. A vinylene compound of the formula I

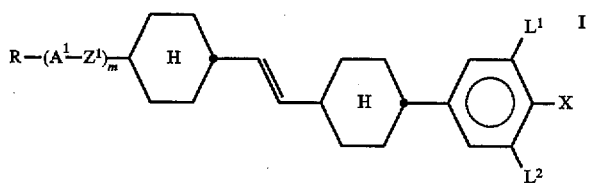

in which

R is an alkenyl radical having 2 to 15 carbon atoms which is unsubstituted, monosubstituted by CN or $CF_3$ or monosubstituted to perhalo-substituted by halogen, in which radicals one or more $CH_2$ groups are optionally, in each case independently of one another, replaced by —O—, —S—,

—CO—, —CO—O, —O—CO— or —O—CO—O— in such a way that oxygen atoms are not linked directly to one another, $A^1$ (a) is a trans-1,4-cyclohexylene radical in which one or more non-adjacent $CH_2$ groups are optionally replaced by —O— and/or —S—,
  (b) is a 1,4-phenylene radical in which one or two CH groups are optionally replaced by N, or
  (c) is a radical selected from the group consisting of 1,4-cyclohexenylene, 1,4-bicyclo[2.2.2]-octylene, piperidine-1,4-diyl, naphthalene-2,6-diyl, decahydronaphthalene-2,6-diyl and 1,2,3,4-tetrahydronaphthalene-2,6-diyl, where the radicals (a) and (b) are optionally substituted one or more times by CN or fluorine, $Z^1$ is —CO—O—, —O—CO—, —$CH_2$O—, —O$CH_2$—, —$CH_2CH_2$—, —CH=CH—, —C≡C— or a single bond, X is CN, OCN, NCS, Cl, F or halogenated alkyl or alkenyl having 1 to 7 carbon atoms, in which one or more non-adjacent $CH_2$ groups are optionally replaced by —O—, $L^1$ and $L^2$ are each independently H or F, and m is 0 or 1.

2. A vinylene compound of claim 1 which is of the formula I1

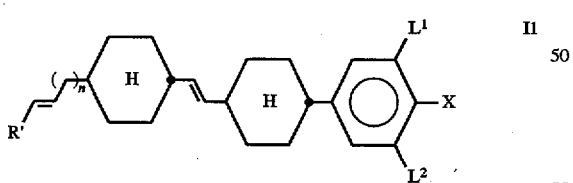

in which
R' is H or n-alkyl having 1–5 carbon atoms,
n is 0–3, and
X, $L^1$ and $L^2$ have the meanings given in claim 1.

3. A vinylene compound according to claim 1, wherein R is —$(CH_2)_n$—CH=CH—R' in which n is 0–3 and R' is H or n-alkyl having 1 to 5 carbon atoms.

4. A vinylene compound according to claim 1, wherein X is CN, F, Cl, $CHF_2$, $OCF_3$, $OCHF_2$, $OCH_2CF_3$, $OCH_2F_5$, $OCF_2CHFCF_3$, $OCHFCHF_2$ or $OCHFCF_3$.

5. A vinylene compound according to claim 1, wherein one or both of $L^1$ and $L^1$ are fluorine.

6. A vinylene compound according to claim 1, wherein $L^1$, $L^2$ and X are fluorine.

7. A vinylene compound of claim 1 which is of the formula I3

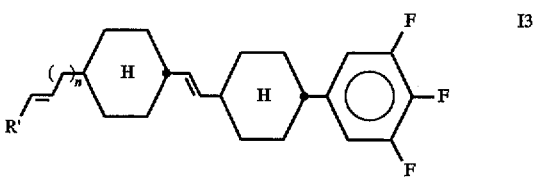

wherein $R^1$ is H or alkyl having 1–5 carbon atoms, and n is 0–3.

8. A liquid-crystalline medium based on a mixture of polar compounds having positive dielectric anisotropy, comprising one or more compounds of the formula I of claim 1.

9. A liquid-crystalline medium according to claim 8, comprising a compound of the formula I3

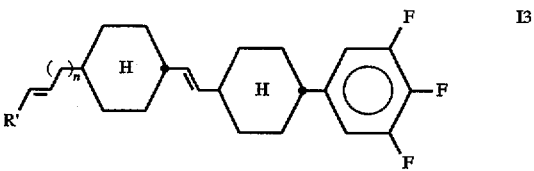

wherein $R^1$ is H or alkyl having 1–5 carbon atoms, and n is 0–3.

10. A liquid crystalline medium according to claim 8, further comprising one or more compounds selected from the group consisting of compounds of the general formulae II to VI

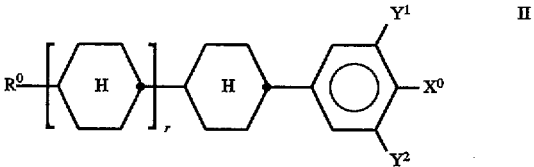

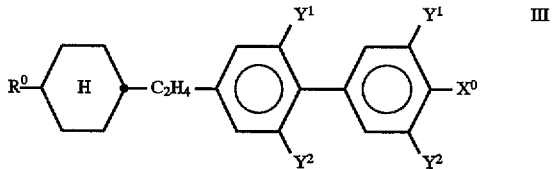

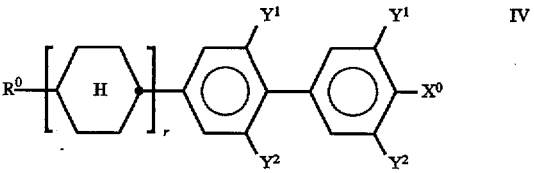

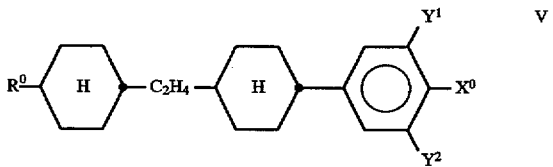

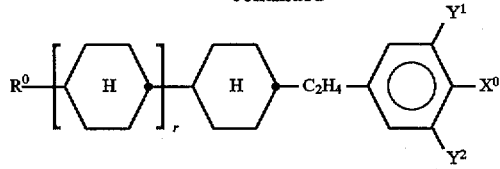

in which

R⁰ is n-alkyl, oxaalkyl, fluoroalkyl or alkenyl having in each case 1 to 9 carbon atoms X⁰ is F, Cl or halogenated alkyl, alkenyl or alkoxy having 1 to 6 carbon atoms $Y^1$ and $Y^2$ are each independently H or F, and r is 0 or 1.

11. A liquid-crystalline medium according to claim 8, comprising one or more compounds of the formula I in which R is a straight-chain alkenyl radical and X is F, CN, $CHF_2$, $OCH_2CF_3$, $OCF_3$, $OCHF_2$, $OCHFCF_3$, $OC_2F_5$, $OCF_2CHFCF_3$ or $OCHFCHF_2$.

12. A liquid-crystalline medium according to claim 8, wherein the proportion of compounds of the formula I in the overall mixture is from 5 to 50% by weight.

13. A liquid-crystalline medium according to claim 10, wherein the proportion of compounds of the formulae II to VI in the overall mixture is from 30 to 70% by weight.

14. An electrooptical liquid-crystal display containing a medium according to claim 8.

15. The vinylene compound of claim 1, wherein R is a straight chain alkenyl radical and radical $A^1$ is 1,4-phenylene, trans-1,4-cyclohexylene, 1,4-cyclohexenylene, pyridine-2,5-diyl or trans-1,3-dioxane-2,5-diyl.

16. The vinylene compound of claim 1, wherein radical $A^1$ is 1,4-phenylene which is mono- or disubstituted by F or mono-substituted by CN.

17. The vinylene compound of claim 1, wherein $Z^1$ is a single bond, —CO—O—, —O—CO— or —CH₂CH₂—.

18. The vinylene compound of claim 1, wherein X is F, Cl or halogenated alkyl.

19. A liquid-crystalline medium of claim 8, wherein the medium retains a nematic phase down to –20 ° C., a clearing point above 80 ° C. and a dielectric anisotropy Δε≧6.

20. A liquid-crystalline medium of claim 8, wherein the medium has a TN threshold below 2.0V.

* * * * *